(12) United States Patent
Fadli

(10) Patent No.: US 9,233,060 B2
(45) Date of Patent: *Jan. 12, 2016

(54) COUPLER WITH 7-AMINO-1,2,3,4-TETRAHYDROQUINOLINE STRUCTURE, DYEING COMPOSITION COMPRISING SAME, PROCESSES AND USES

(71) Applicant: L'OREAL, Paris (FR)

(72) Inventor: Aziz Fadli, Chelles (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/365,722

(22) PCT Filed: Dec. 17, 2012

(86) PCT No.: PCT/EP2012/075810
§ 371 (c)(1),
(2) Date: Jun. 16, 2014

(87) PCT Pub. No.: WO2013/087932
PCT Pub. Date: Jun. 20, 2013

(65) Prior Publication Data
US 2015/0000691 A1    Jan. 1, 2015

Related U.S. Application Data

(60) Provisional application No. 61/584,983, filed on Jan. 10, 2012.

(30) Foreign Application Priority Data

Dec. 16, 2011  (FR) ..................................... 11 61795

(51) Int. Cl.
| | |
|---|---|
| *A61Q 5/10* | (2006.01) |
| *A61K 8/49* | (2006.01) |
| *C07D 403/12* | (2006.01) |
| *C07D 215/38* | (2006.01) |
| *C07D 401/06* | (2006.01) |
| *C07D 403/06* | (2006.01) |
| *C07D 413/06* | (2006.01) |
| *C07D 413/12* | (2006.01) |
| *C07D 471/10* | (2006.01) |

(52) U.S. Cl.
CPC ................. *A61K 8/4946* (2013.01); *A61K 8/49* (2013.01); *A61K 8/494* (2013.01); *A61K 8/4926* (2013.01); *A61Q 5/10* (2013.01); *C07D 215/38* (2013.01); *C07D 401/06* (2013.01); *C07D 403/06* (2013.01); *C07D 403/12* (2013.01); *C07D 413/06* (2013.01); *C07D 413/12* (2013.01); *C07D 471/10* (2013.01); *A61K 2800/43* (2013.01); *A61K 2800/87* (2013.01)

(58) Field of Classification Search
CPC .......... A61Q 5/10; A61K 8/49; A61K 8/494; A61K 8/4926; A61K 8/4946; A61K 2800/87; C07D 403/06; C07D 403/12; C07D 401/06; C07D 413/12; C07D 215/38; C07D 413/06
USPC .......................................................... 8/405
See application file for complete search history.

(56) References Cited

U.S. PATENT DOCUMENTS

| | | |
|---|---|---|
| 4,003,699 A | 1/1977 | Rose et al. |
| RE30,199 E | 1/1980 | Rose et al. |
| 4,823,985 A | 4/1989 | Grollier et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Mockli |
| 5,766,576 A | 6/1998 | Lowe et al. |

(Continued)

FOREIGN PATENT DOCUMENTS

| | | |
|---|---|---|
| DE | 2359399 A1 | 5/1975 |
| DE | 2941512 A1 | 4/1980 |

(Continued)

OTHER PUBLICATIONS

English abstract of the Patent No. DE 10103657 A1 dated (2002).*

(Continued)

*Primary Examiner* — Eisa Elhilo
(74) *Attorney, Agent, or Firm* — The Marbury Law Group, PLLC

(57) ABSTRACT

The invention relates to the use of specific heterocyclic couplers which are 7-amino-1,2,3,4-tetrahydroquinoline derivatives of formula (I) for dyeing keratin fibers such as the hair in which formula (I): $R_1$ to $R_6$, $R_a$ to $R_c$ and X are as defined in the description.

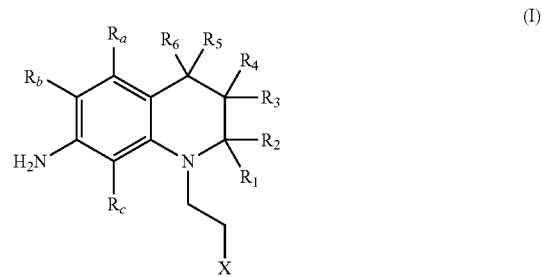

(I)

15 Claims, No Drawings

(56) References Cited

U.S. PATENT DOCUMENTS

| | | | |
|---|---|---|---|
| 6,099,592 | A | 8/2000 | Vidal et al. |
| 6,099,593 | A | 8/2000 | Terranova et al. |
| 6,248,137 | B1 | 6/2001 | Terranova et al. |
| 6,284,003 | B1 | 9/2001 | Rose et al. |
| 6,338,741 | B1 | 1/2002 | Vidal et al. |
| 6,645,258 | B2 | 11/2003 | Vidal et al. |
| 6,730,789 | B1 | 5/2004 | Birault et al. |
| 6,783,557 | B1 | 8/2004 | Terranova et al. |
| 7,981,903 | B2 | 7/2011 | Chamberlain et al. |
| 2001/0020310 | A1 | 9/2001 | Terranova et al. |
| 2002/0050013 | A1 | 5/2002 | Vidal et al. |
| 2003/0019051 | A9 | 1/2003 | Vidal et al. |
| 2005/0166335 | A1 | 8/2005 | Vidal et al. |
| 2006/0258689 | A1 | 11/2006 | Kelly et al. |
| 2007/0136959 | A1 | 6/2007 | Fadli |
| 2007/0143935 | A1 | 6/2007 | Fadli et al. |
| 2008/0071092 | A1 | 3/2008 | Vidal et al. |
| 2008/0234237 | A1 | 9/2008 | Maddaford et al. |
| 2010/0115711 | A1 | 5/2010 | Fadli et al. |
| 2010/0204196 | A1 | 8/2010 | Chamberlain et al. |

FOREIGN PATENT DOCUMENTS

| | | | | |
|---|---|---|---|---|
| DE | 3843892 | A1 | 6/1990 | |
| DE | 4133957 | A1 | 4/1993 | |
| DE | 19543988 | A1 | 5/1997 | |
| DE | 10103657 | A1 * | 8/2002 | ............... A61K 7/13 |
| EP | 0714954 | A2 | 6/1996 | |
| EP | 0770375 | A1 | 5/1997 | |
| EP | 0926149 | A1 | 6/1999 | |
| EP | 1792606 | A1 | 6/2007 | |
| EP | 1792903 | A1 | 6/2007 | |
| FR | 2586913 | A1 | 3/1987 | |
| FR | 2733749 | | 11/1996 | |
| FR | 2801308 | | 5/2001 | |
| FR | 2866338 | A1 | 8/2005 | |
| FR | 2927078 | A1 | 8/2009 | |
| GB | 1026978 | | 4/1966 | |
| GB | 1153196 | | 5/1969 | |
| GB | 2036777 | A | 7/1980 | |
| JP | 219576 | | 1/1990 | |
| JP | 5163124 | | 6/1993 | |
| WO | 9408969 | A1 | 4/1994 | |
| WO | 9408970 | A1 | 4/1994 | |
| WO | 9501772 | A1 | 1/1995 | |
| WO | 9515144 | A1 | 6/1995 | |
| WO | 9615765 | A1 | 5/1996 | |
| WO | 9749378 | A1 | 12/1997 | |
| WO | 9847868 | A1 | 10/1998 | |
| WO | 0006146 | A1 | 2/2000 | |
| WO | 0043396 | A1 | 7/2000 | |
| WO | 03068749 | A1 | 8/2003 | |
| WO | 2005023807 | A2 | 3/2005 | |
| WO | 2008025240 | A1 | 3/2008 | |
| WO | 2009020990 | A1 | 2/2009 | |
| WO | 2009098257 | A1 | 8/2009 | |
| WO | 2011107501 | A1 | 9/2011 | |
| WO | 2011110627 | A1 | 9/2011 | |
| WO | 2013087931 | A1 | 6/2013 | |

OTHER PUBLICATIONS

International Search Report for PCT/EP2012/075810, (2012).
English language abstract for DE 10103657, (2002).
English language abstract for EP 0770375, (1997).
English language abstract for JP 2-19576, (1990).
English language abstract for JP 5-163124, (1993).
Bilski, P.J. et. al., "Quenching and Generation of Singlet Oxygen by Hydroethidine and Related Chromophores," Chemical Physics Letters, Elsevier BV, NL., Jun. 16, 2009, vol. 475, No. 1-3, pp. 116-119.

* cited by examiner

COUPLER WITH 7-AMINO-1,2,3,4-TETRAHYDROQUINOLINE STRUCTURE, DYEING COMPOSITION COMPRISING SAME, PROCESSES AND USES

CROSS REFERENCE TO RELATED APPLICATIONS

This is a national stage application of PCT/EP2012/075810, filed internationally on Dec. 17, 2012, which claims priority to U.S. Provisional Application No. 61/584,983, filed on Jan. 10, 2012, as well as French Application No. 1161795, filed Dec. 16, 2011.

The subject of the present application is specific 7-amino-1,2,3,4-tetrahydroquinoline derivatives, the use thereof for dyeing keratin fibres, in particular human keratin fibres such as the hair, the dyeing compositions comprising such 7-amino-1,2,3,4-tetrahydroquinolines and also the processes and devices using these tetrahydroquinolines.

It is known practice to dye keratin fibres, and especially human hair, with dyeing compositions containing oxidation dye precursors, generally called oxidation bases, such as ortho- or para-phenylenediamines, ortho- or para-aminophenols and heterocyclic compounds. These oxidation bases are colourless or weakly coloured compounds which, when combined with oxidizing products, are able to produce coloured compounds by a process of oxidative condensation.

It is also known that the shades obtained with these oxidation bases can be varied by combining them with couplers or coloration modifiers, the latter being selected more particularly from aromatic meta-diaminobenzenes, meta-aminophenols, meta-diphenols and certain heterocyclic compounds such as indole compounds.

The variety of the molecules used as oxidation bases and couplers allows a rich palette of colours to be obtained.

The "permanent" dyeing obtained by means of these oxidation dyes must moreover satisfy a certain number of requirements. Thus, it should have no toxicological drawbacks, it should allow shades to be obtained in the desired intensity, and it should show good resistance to external agents such as light, bad weather, washing, permanent waving treatments, perspiration and rubbing.

The dyes are also required to cover white hairs, and to be as unselective as possible, that is to say to produce the smallest possible differences in coloration along a single lock of keratin fibre, which in general has a sensitivity (that is to say damage) which differs between its end and its root.

Heterocyclic oxidation bases make it possible to obtain a broad palette of colours, but combinations thereof with conventional couplers sometimes lack homogeneity and chromaticity and there is often considerable selectivity.

Certain 7-amino-1,2,3,4-tetrahydroquinoline derivatives are known as dyes for polyesters (DE 294 1512). Other derivatives have been used for therapeutic application thereof (see, for example: vaniloid receptor modulator: WO 2003/068749; $5HT_{1A}$, $5HT_{1B}$, $HT_{1D}$ receptor antagonists: WO 98/47868; capsaicin receptor modulator: WO 2005/023807, NO inhibitor: US20080234237, and CCR5 receptor agonist or antagonist: WO 00/06146).

In hair dyeing, it is known practice to use 7-amino-1,2,3,4-tetrahydroquinoline derivatives as couplers (WO 2008/025240). Nevertheless, the colorations obtained with these couplers are not always satisfactory. Indeed, whether in terms of solubility, of colour uptake, of chromaticity, of fastness, of persistence (washing, bad weather, light) and/or of colour selectivity (root/end colour "homogeneity"), these couplers do not always give the user satisfaction.

These technical problems have been solved by the use of specific heterocyclic couplers which are 7-amino-1,2,3,4-tetrahydroquinoline derivatives of formula (I) for dyeing keratin fibres such as the hair; compound of formula (I) and also the salts thereof with an organic or inorganic acid or base, the optical or geometric isomers thereof and/or the solvates thereof such as the hydrates:

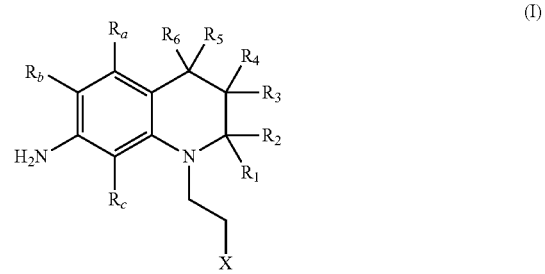

(I)

in which formula (I):

$R_1$, $R_2$, $R_3$, $R_4$, $R_5$ and $R_6$, which may be identical or different, represent a hydrogen or halogen atom; a linear or branched $C_1$-$C_6$ alkyl radical optionally substituted with one or more hydroxyl groups, preferably with a single hydroxyl group; a carboxyl radical; a ($C_1$-$C_6$) alkoxycarbonyl radical —C(O)—O—R with R representing a linear or branched $C_1$-$C_6$ alkyl radical; an alkylcarbonyloxy radical —O—C(O)—R with R being as defined previously; preferably, $R_1$, $R_2$, $R_3$, $R_4$, $R_5$ and $R_6$, which may be identical or different, represent a hydrogen atom or a $C_1$-$C_4$ alkyl radical; even more advantageously, $R_1$, $R_2$, $R_3$, $R_4$, $R_5$ and $R_6$ are identical and represent a hydrogen atom;

$R_a$, $R_b$ and $R_c$, which may be identical or different, represent a hydrogen or halogen atom or a $C_1$-$C_6$ alkyl radical; preferably, $R_a$, $R_b$ and $R_c$ are identical and represent a hydrogen atom;

X represents i) an amino radical —$NT_1T_2$, ii) an aminoalkylamino radical —$N(T_3)$-L-$NT_1T_2$ or iii) an oxyalkylamino radical —O-L-$NT_1T_2$;

$T_1$ and $T_2$, which may be identical or different, represent a linear or branched $C_1$-$C_6$ alkyl radical optionally substituted with one or more hydroxyl radicals, preferably with a single hydroxyl group;

or else $T_1$ and $T_2$ together form, with the nitrogen atom to which they are attached, a (non-cationic) saturated or unsaturated heterocycle comprising 5 to 7 members, one of the members of which may be a heteroatom chosen from O, S and N; it being possible for said heterocycle to be optionally substituted with one or more linear or branched $C_1$-$C_4$ alkyl or linear or branched $C_1$-$C_4$ hydroxyalkyl radicals;

$T_3$ represents a hydrogen atom or a linear or branched $C_1$-$C_6$ alkyl radical optionally substituted with one or more hydroxyl radicals, preferably with a single hydroxyl group;

L represents a linear or branched, saturated $C_1$-$C_{10}$ alkylene hydrocarbon-based chain optionally substituted with one or more hydroxyl radicals, preferably with a single hydroxyl group.

A subject of the invention is also a process for dyeing keratin fibres using the compounds of formula (I) as defined previously.

A subject of the invention is also novel heterocyclic couplers which are 7-amino-1,2,3,4-tetrahydroquinoline derivatives of formula (I) as defined previously, it being understood that the compounds of formula (I) cannot represent the following compounds (A), (B), (C) or (D):

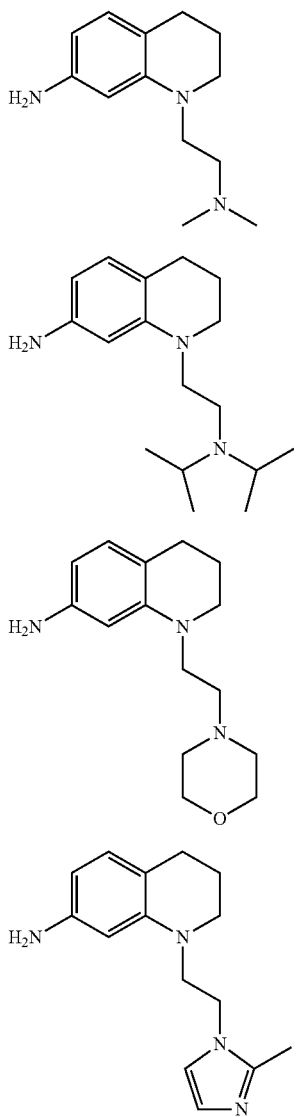

A subject of the invention is also a process for synthesizing novel compounds of formula (I), and also a cosmetic composition comprising the compounds of formula (I) as defined previously, with the exception of the compounds (A), (B), (C), and (D) as defined previously.

A subject of the invention is also a multi-compartment kit or device comprising at least one compound of formula (I) as defined previously.

The couplers according to the invention result in a wide range of colours in oxidation dyeing. These couplers make it possible in particular to expand the colour range while improving the innocuousness of the oxidation dyeing couplers. In addition, these 7-amino-1,2,3,4-tetrahydroquinoline derivatives make it possible to obtain colorations in varied shades, in particular dark, natural, natural dark, powerful and chromatic shades.

These colorations are also sparingly selective and they are persistent; they withstand well the various attacks that the fibres may experience.

These heterocyclic couplers exhibit, furthermore, a high solubility, which allows a satisfactory uptake of the colour.

Other characteristics, aspects, subjects and advantages of the present invention will emerge even more clearly on reading the description and the examples that follow.

In the text hereinbelow, unless otherwise indicated, the limits of a range of values are included in that range, especially in the expressions "between" and "ranging from . . . to . . . ".

In the text hereinbelow, the expression "at least one" is equivalent to the expression "one or more".

Compound of Formula (I)

The present invention relates to 7-amino-1,2,3,4-tetrahydroquinoline derivatives of general formula (I) as defined previously, and also the salts thereof with an organic or inorganic acid or base, the optical or geometric isomers thereof and/or the solvates thereof such as the hydrates.

The compounds of formula (I) may comprise a heterocyclic radical. By way of example of a saturated or unsaturated, 5- to 7-membered heterocyclic radical, one of the members of which may be a heteroatom chosen from O, S or N, mention may be made of imidazole, pyridine, piperazine, pyrrolidine, morpholine, pyrimidine, thiazole, benzimidazole, benzothiazole, oxazole and benzotriazole rings, and pyrazoliums, triazoles, benzoxazoles and piperidines.

According to one particular mode of the invention, the compounds of formula (I) are such that X represents i) an amino radical —$NT_1T_2$.

In particular, $T_1$ and $T_2$ denote, independently of one another, a linear or branched $C_1$-$C_4$ alkyl radical optionally substituted with one or more hydroxyl radicals, preferably with one hydroxyl, or else $T_1$ and $T_2$ together form, with the nitrogen atom which bears them, a heterocycle chosen from imidazole, pyridine, piperazine, pyrrolidine, morpholine, pyrimidine, benzimidazole and piperidine; said heterocycle being optionally substituted with one or more linear or branched $C_1$-$C_4$ alkyl or $C_1$-$C_4$ hydroxyalkyl radicals.

Preferably, $T_1$ and $T_2$ independently denote a linear $C_1$-$C_4$ alkyl radical, such as methyl or ethyl.

According to one particular mode of the invention, the radical X represents an amino radical —$NT_1T_2$ with $T_1$ and $T_2$ together forming, with the nitrogen atom which bears them, a (non-cationic) heterocycle chosen from imidazole, piperazine, pyrrolidine, morpholine and piperidine; said heterocycle being optionally substituted with one or more linear or branched $C_1$-$C_4$ alkyl or $C_1$-$C_4$ hydroxyalkyl radicals; preferably, when $T_1$ and $T_2$ form, with the nitrogen atom to which they are attached, a (non-cationic) heterocycle, this heterocycle is chosen from 4-methylpiperazino, imidazole, pyrrolidino, piperidino and morpholino.

According to another particular mode of the invention, the compounds of formula (I) are such that X represents ii) a radical —$N(T_3)$-L-$NT_1T_2$.

In particular, taken together or separately, $T_1$ and $T_2$ independently denote a linear or branched $C_1$-$C_4$ alkyl radical optionally substituted with one or more hydroxyl radicals, preferably with one hydroxyl, and/or $T_3$ denotes a hydrogen atom or a linear or branched $C_1$-$C_4$ alkyl radical; or $T_1$ and $T_2$ form, with the nitrogen atom to which they are attached, a heterocycle chosen from imidazole, pyridine, piperazine, pyrrolidine, morpholine, pyrimidine, benzimidazole and piperidine; said heterocycle being optionally substituted with one or more linear or branched $C_1$-$C_4$ alkyl or $C_1$-$C_4$ hydroxyalkyl radicals; and/or L denotes a linear, saturated $C_1$-$C_6$ alkylene hydrocarbon-based chain optionally substituted with one or more hydroxyl radicals, preferably with one hydroxyl.

More particularly, according to this variant, $T_1$ and $T_2$ independently denote a linear $C_1$-$C_4$ alkyl radical, such as methyl or ethyl; or else $T_1$ and $T_2$ together form, with the nitrogen atom which bears them, a (non-cationic) heterocycle chosen from imidazole, piperazine, pyrrolidine, morpholine and piperidine; said heterocycle being optionally substituted with one or more linear or branched $C_1$-$C_4$ alkyl or $C_1$-$C_4$ hydroxyalkyl radicals; preferably, when $T_1$ and $T_2$ form, with the nitrogen atom to which they are attached, a (non-cationic) heterocycle, this heterocycle is chosen from 4-methylpiperazino, imidazole, pyrrolidino, piperidino and morpholino;

$T_3$ denotes a hydrogen atom or a linear $C_1$-$C_4$ alkyl radical, such as methyl; and/or L denotes a —$(CH_2)_p$— alkylene chain with p representing an integer inclusively between 1 and 6, preferably p=2, 3 or 4.

According to another particular mode of the invention, the compounds of formula (I) are such that X represents iii) a radical —O-L-$NT_1T_2$.

In particular, taken together or separately:

$T_1$ and $T_2$ independently denote a linear or branched $C_1$-$C_4$ alkyl radical optionally substituted with one or more hydroxyl radicals, preferably with one hydroxyl; or $T_1$ and $T_2$ together form, with the nitrogen atom which bears them, a heterocycle chosen from imidazole, pyridine, piperazine, pyrrolidine, morpholine, pyrimidine, benzimidazole and piperidine; said heterocycle being optionally substituted with one or more linear or branched $C_1$-$C_4$ alkyl or $C_1$-$C_4$ hydroxyalkyl radicals; and/or L denotes a linear, saturated $C_1$-$C_6$ alkylene hydrocarbon-based chain optionally substituted with one or more hydroxyl radicals.

More particularly, according to this variant, $T_1$ and $T_2$ independently denote a linear $C_1$-$C_4$ alkyl radical, such as methyl or ethyl; or else $T_1$ and $T_2$ together form, with the nitrogen atom which bears them, a (non-cationic) heterocycle chosen from imidazole, piperazine, pyrrolidine, morpholine and piperidine; said heterocycle being optionally substituted with one or more linear or branched $C_1$-$C_4$ alkyl or $C_1$-$C_4$ hydroxyalkyl radicals; preferably, when $T_1$ and $T_2$ form, with the nitrogen atom to which they are attached, a (non-cationic) heterocycle, this heterocycle is chosen from 4-methylpiperazino, imidazole, pyrrolidino, piperidino and morpholino; and/or L denotes a —$(CH_2)_p$— alkylene chain with p representing an integer inclusively between 1 and 6, preferably p=2, 3 or 4.

The compounds of formula (I) may be in the form of a salt of an organic or inorganic acid or base.

The term "salt of an organic or inorganic acid" is intended to mean more particularly those chosen from addition salts with a cosmetically acceptable acid, such as the acidifying agents as defined hereinafter, for instance the salts derived i) from hydrochloric acid HCl, ii) from hydrobromic acid HBr, iii) from sulfuric acid $H_2SO_4$, iv) from alkylsulfonic acids: Alk-$S(O)_2OH$ such as methlysulfonic acid and ethylsulfonic acid; v) from arylsulfonic acids: Ar—$S(O)_2OH$ such as benzenesulfonic acid and toluenesulfonic acid; vi) from citric acid; vii) from succinic acid; viii) from tartaric acid; ix) from lactic acid; x) from alkoxysulfinic acids: Alk-O—$S(O)OH$ such as methoxysulfinic acid and ethoxysulfinic acid; xi) from aryloxysulfinic acids such as tolueneoxysulfinic acid and phenoxysulfinic acid; xii) from phosphoric acid $H_3PO_4$; xiii) from acetic acid $CH_3C(O)OH$; xiv) from triflic acid $CF_3SO_3H$ and xv) from tetrafluoroboric acid $HBF_4$. More particularly, the compounds of formula (I) are optionally salified with strong inorganic acids, such as HCl, HBr, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

The term "salt of an organic or inorganic base" is intended to mean more particularly those chosen from addition salts with a cosmetically acceptable base, such as the alkalinizing agents as defined below, for instance alkali metal hydroxides such as sodium hydroxide or potassium hydroxide, aqueous ammonia, amines or alkanolamines.

The compounds of formula (I) may also be in the form of solvates, for example a hydrate or a solvate of a linear or branched alcohol such as ethanol or isopropanol.

In the context of the invention, the term "derivative of formula (I)" is understood to mean all mesomeric, tautomeric or optical isomeric forms.

Particularly in the context of the invention, compounds of formula (I) are not cationic. In other words compounds of formula (I) do not bear a permanent cationic charge independently of the pH medium.

Preferably, the 7-amino-1,2,3,4-tetrahydroquinolines of general formula (I) used for dyeing keratin fibres are chosen from the following compounds:

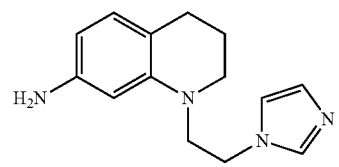

1-[2-(1H-imidazol-1-yl)ethyl]-1,2,3,4-tetrahydroquinolin-7-amine

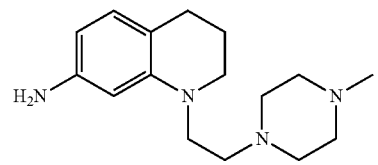

1-[2-(4-methylpiperazin-1-yl)ethyl]-1,2,3,4-tetrahydroquinolin-7-amine

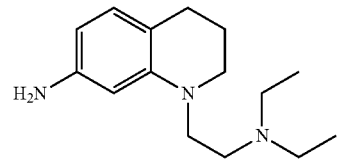

1-[2-(diethylamino)ethyl]-1,2,3,4-tetrahydroquinolin-7-amine

-continued

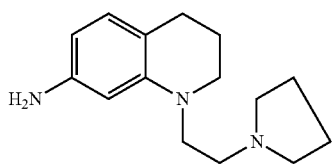
1-[2-(pyrrolidin-1-yl)ethyl]-1,2,3,4-
tetrahydroquinolin-7-amine

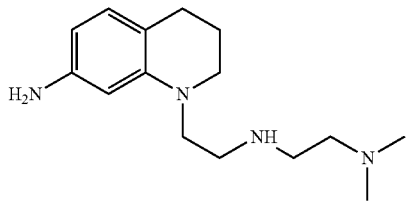
N'-[2-(7-amino-3,4-dihydroquinolin-
1(2H)-yl)ethyl]-N,N-dimethylethane-
1,2-diamine

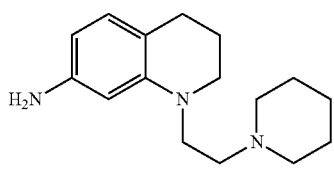
1-[2-(piperidin-1-yl)ethyl]-1,2,3,4-
tetrahydroquinolin-7-amine

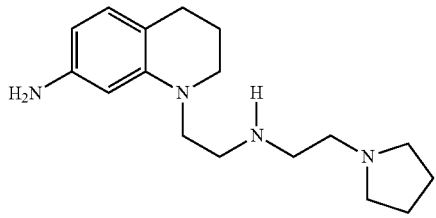
1-(2-{[2-(pyrrolidin-1-yl)ethyl]amino}ethyl)-
1,2,3,4-tetrahydroquinolin-7-amine

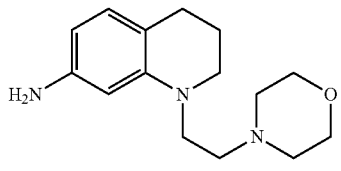
1-[2-(morpholin-4-yl)ethyl]-1,2,3,4-
tetrahydroquinolin-7-amine

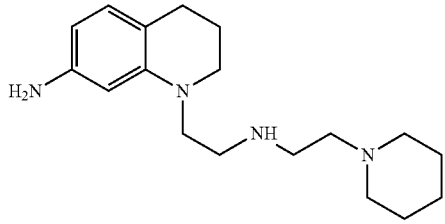
1-(2-{[2-(piperidin-1-yl)ethyl]amino}ethyl)-
1,2,3,4-tetrahydroquinolin-7-amine -continued

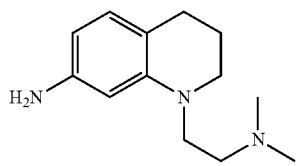
1-[2-(dimethylamino)ethyl]-1,2,3,4-
tetrahydroquinolin-7-amine

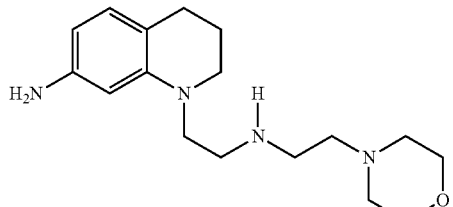
1-(2-{[2-(morpholin-4-yl)ethyl]amino}ethyl)-
1,2,3,4-tetrahydroquinolin-7-amine

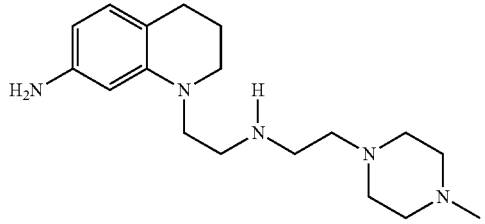
1-(2-{[2-(4-methylpiperazin-1-yl)ethyl]amino}ethyl)-
1,2,3,4-tetrahydroquinolin-7-amine

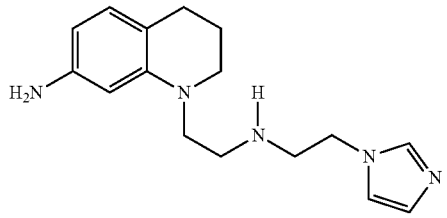
1-(2-{[2-(1H-imidazol-1-yl)ethyl]amino}ethyl)-
1,2,3,4-tetrahydroquinolin-7-amine

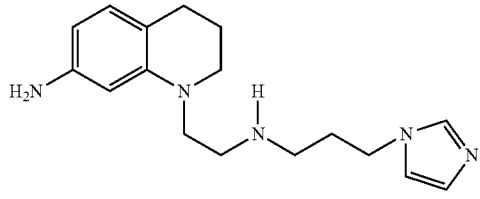
1-(2-{[3-(1H-imidazol-1-yl)propyl]amino}ethyl)-
1,2,3,4-tetrahydroquinolin-7-amine

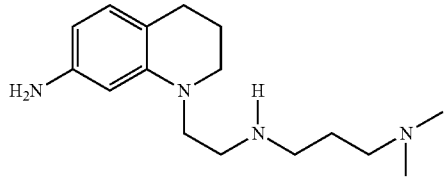
N'-[2-(7-amino-3,4-dihydroquinolin-
1(2H)-yl)ethyl]-N,N-dimethylpropane-
1,3-diamine

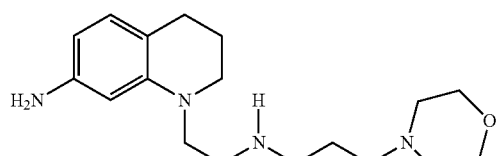

1-(2-{[3-(morpholin-4-yl)propyl]amino}ethyl)-
1,2,3,4-tetrahydroquinolin-7-amine

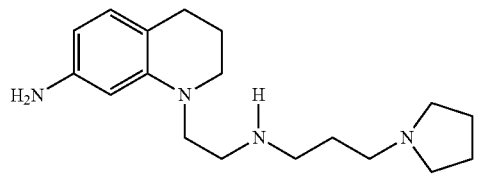

1-(2-{[3-(pyrrolidin-1-yl)propyl]amino}ethyl)-
1,2,3,4-tetrahydroquinolin-7-amine

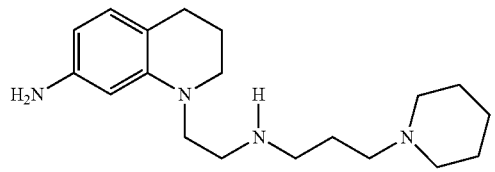

1-(2-{[3-(piperidin-1-yl)propyl]amino}ethyl)-
1,2,3,4-tetrahydroquinolin-7-amine

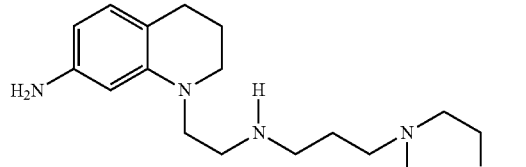

1-(2-{[3-(4-methylpiperazin-1-yl)propyl]amino}ethyl)-
1,2,3,4-tetrahydroquinolin-7-amine

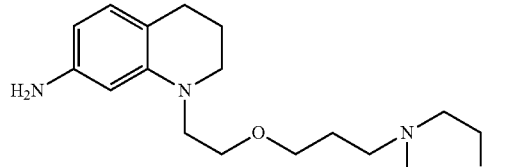

1-(2-{[3-(4-methylpiperazin-1-yl)propoxy]ethyl}-
1,2,3,4-tetrahydroquinolin-7-amine

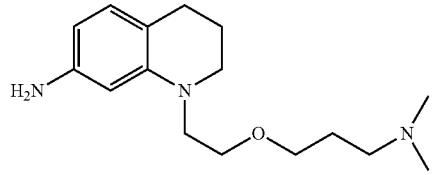

1-{2-[3-(dimethylamino)propoxy]ethyl}-
1,2,3,4-tetrahydroquinolin-7-amine

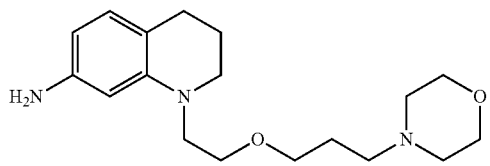

1-{2-[3-(morpholin-4-yl)propoxy]ethyl}-
1,2,3,4-tetrahydroquinolin-7-amine

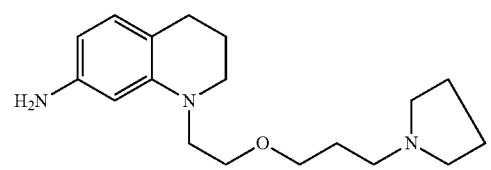

1-{2-[3-(pyrrolidin-1-yl)propoxy]ethyl}-
1,2,3,4-tetrahydroquinolin-7-amine

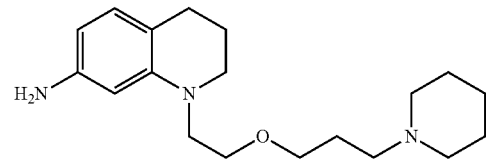

1-{2-[3-(piperidin-1-yl)propoxy]ethyl}-
1,2,3,4-tetrahydroquinolin-7-amine

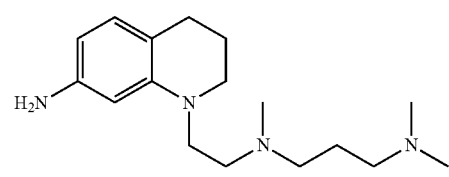

N-[2-(7-amino-3,4-dihydroquinolin-
1(2H)-yl)ethyl]-N,N',N'-trimethyl-
propane-1,3-diamine

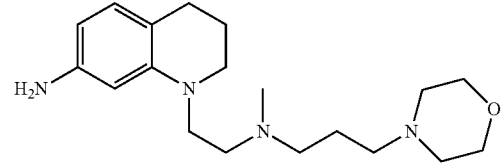

1-(2-{methyl[3-(morpholin-4-yl)propyl]-
amino}ethyl)-1,2,3,4-tetrahydro-
quinolin-7-amine

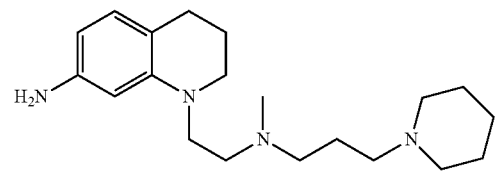

1-(2-{methyl[3-(piperidin-1-
yl)propyl]amino}ethyl)-1,2,3,4-
tetrahydroquinolin-7-amine -continued

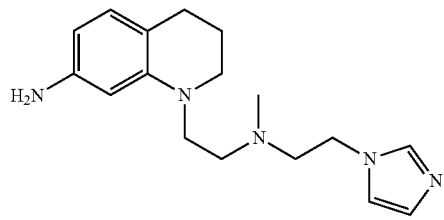

28

1-(2-{[2-(1H-imidazol-1-yl)ethyl](methyl)amino}ethyl)-1,2,3,4-tetrahydroquinolin-7-amine Compounds 1 to 28 and also the salts thereof with organic or inorganic acids or bases, and/or the solvates thereof.

According to one variant, the compounds of formula (I) are such that X represents i) a radical $-NT_1T_2$, the preferred compounds are then of formulae 1, 2, 3, 4 and 6.

According to another variant, the compounds of formula (I) are such that X represents ii) a radical $-N(T_3)-L-NT_1T_2$; the preferred compounds are then of formulae 5, 7, 9, 11, 12, 13, 14, 15, 16, 17, 18, 19, 25, 26, 27 and 28.

According to yet another variant, the compounds of formula (I) are such that X represents iii) a radical $-O-L-NT_1L_2$, the preferred compounds are then of formulae 20, 21, 22, 23 and 24.

According to one particular embodiment, the synthesis of the compounds of formula (I) may be carried out according to the following scheme (1):

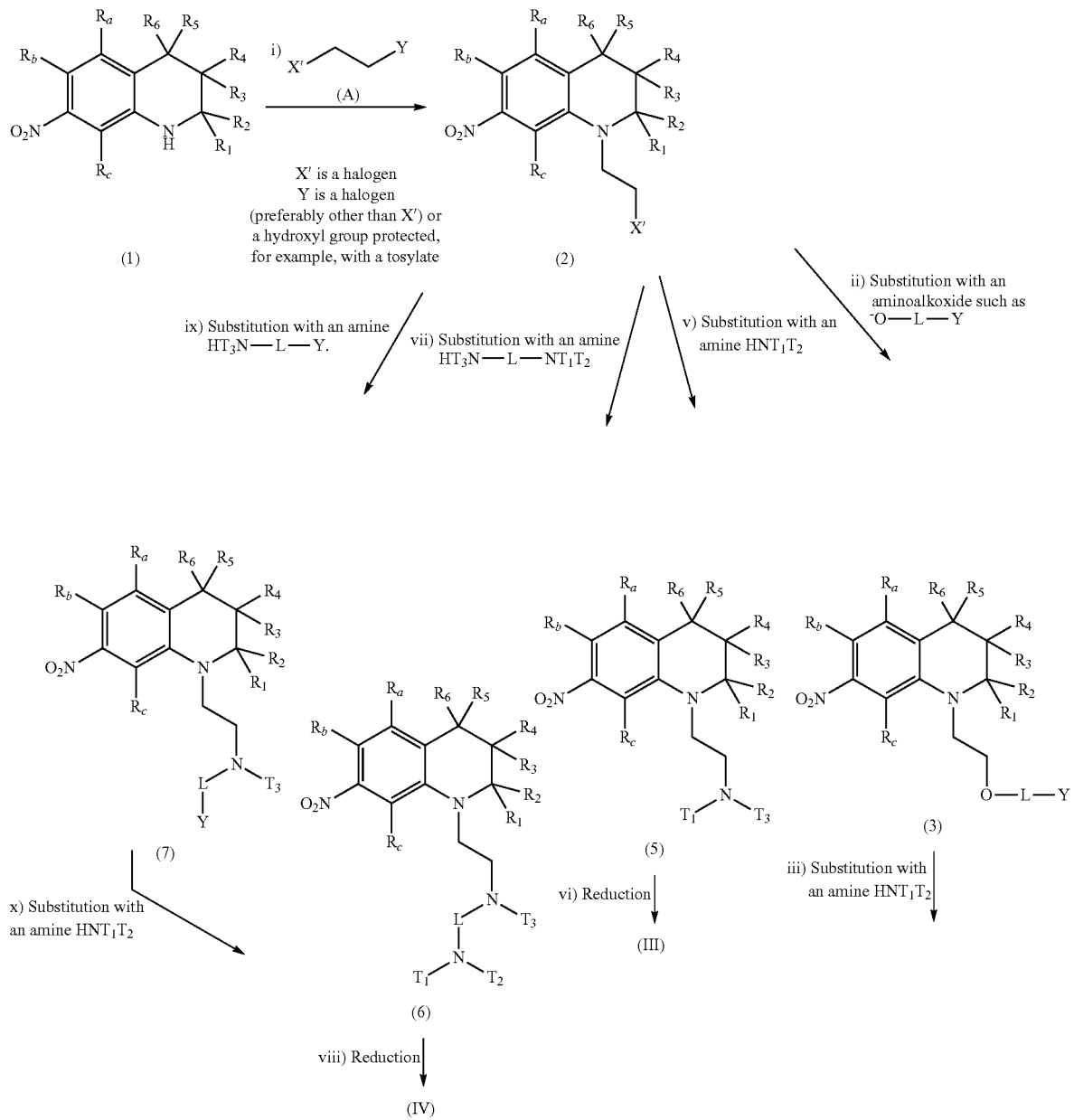

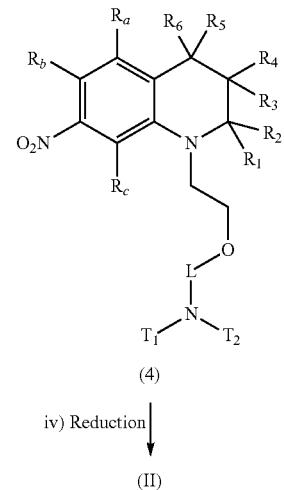
(4)
iv) Reduction ↓
(II)
According to this reaction scheme, the following compounds of formula (II), (III) or (IV), belonging to the compounds of formula (I), are obtained.
It is also possible to obtain the compounds of formulae (II), (III) and (IV) according to schemes (2), (3) and (4), respectively, below.
Scheme (2)
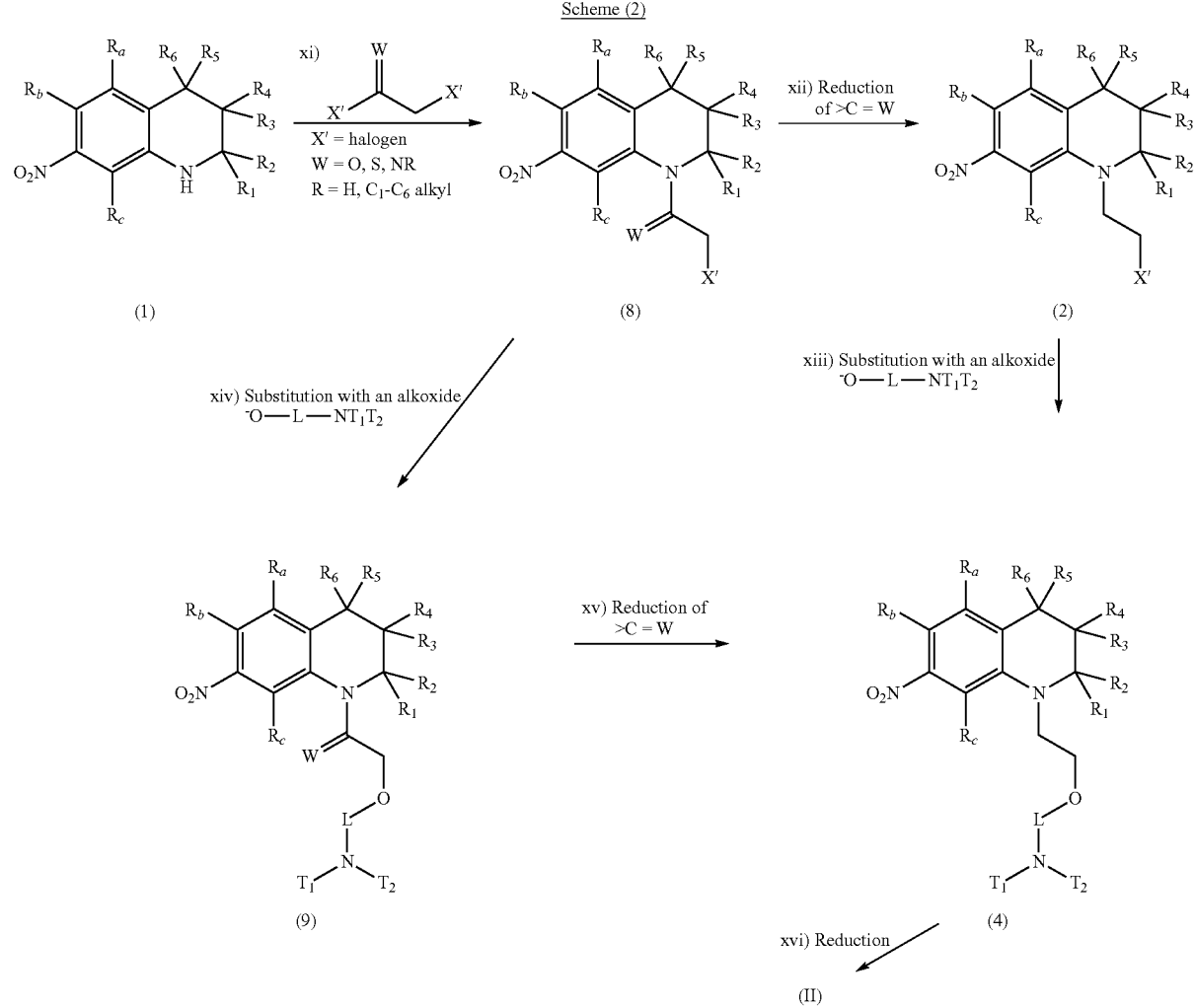

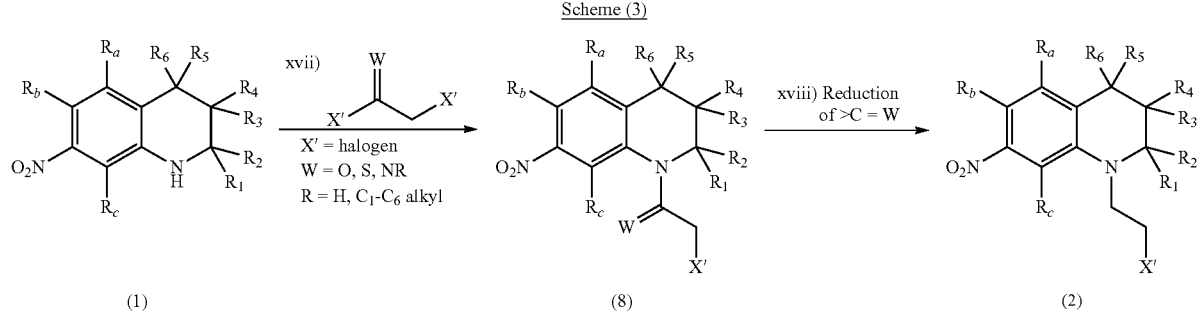
Scheme (3)
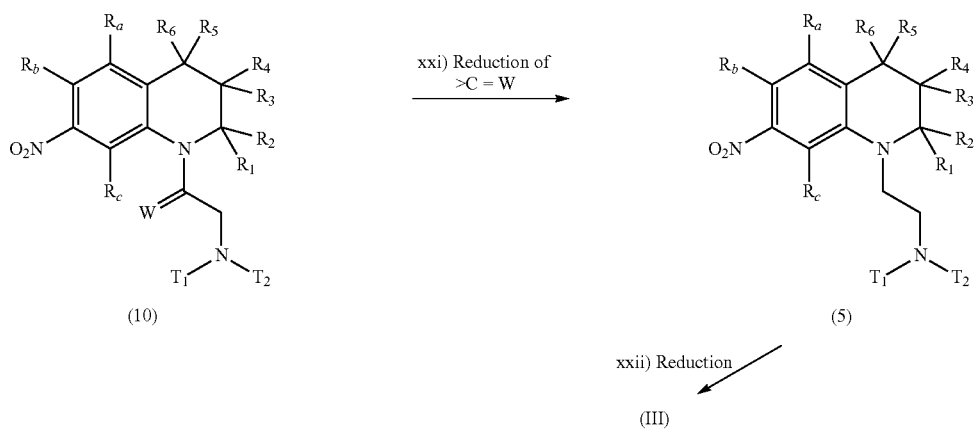
Scheme (4)
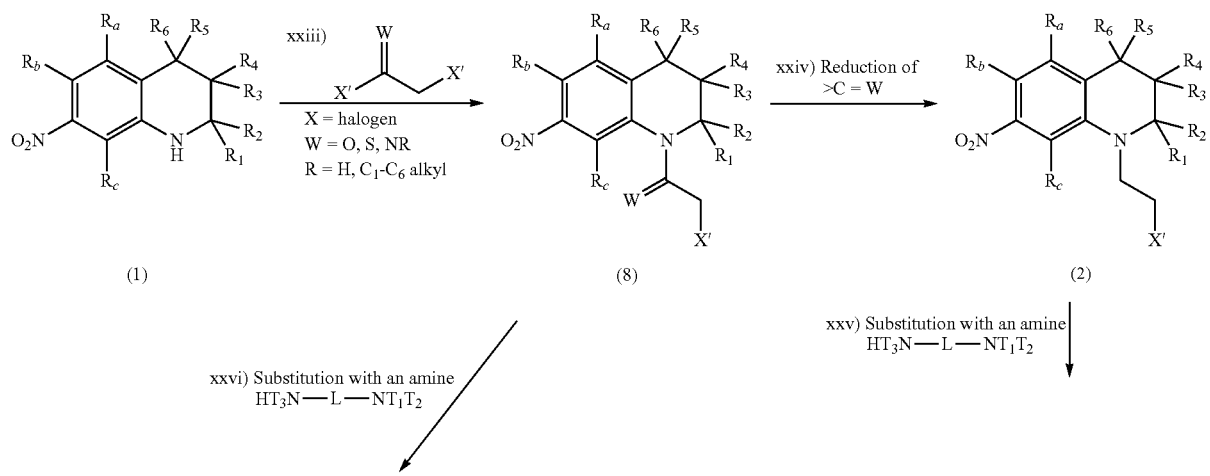

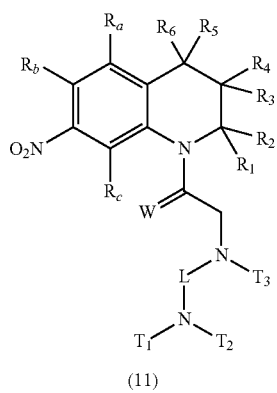

(11)

xxvii) Reduction of >C=W

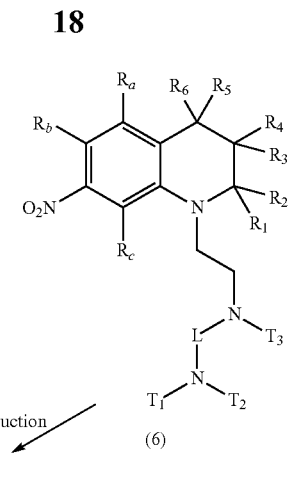

xxviii) Reduction (IV)

(6)

according to schemes (1) to (4) above, the first step is a conventional reaction of N-substitution of the 7-nitro-1,2,3,4-tetrahydroquinoline (1):

- by "alkylation" using reactant (A) $X'$—$CH_2$—$CH_2$—Y, with $X'$ and Y, which may be identical or different, preferably different, representing a leaving or nucleofuge group such as a halogen atom, for instance chlorine, bromine or iodine, or a protected hydroxyl group such as mesylate, tosylate or triflate, preferably tosylate (scheme (1), pathway i)) so as to give the intermediate (2); or else
- by "acylation" using the reactant $X'$—C(W)—$CH_2$—$X'$, with $X'$, which may be identical or different, representing a halogen atom such as chlorine or bromine, W representing an oxygen or sulfur atom or an NR group, with R representing a hydrogen atom or a linear or branched ($C_1$-$C_6$) alkyl group, preferably W=oxygen, (scheme (2), pathway xi), scheme (3), pathway xvii) and scheme (4), pathway xxxiii)) so as to give the intermediate (8);

the intermediate (2) comprising a nucleofuge group $X'$ can then:

- either undergo nucleophilic substitution with an alkoxide Y-L-O⁻, M⁺ with Y as defined previously and L as defined previously and M⁺ representing an alkali metal or an alkaline-earth metal, such as Na, K or Li, so as to give the intermediate (3) which comprises a nucleofuge group Y (scheme (1), pathway ii)), it being possible for the latter to undergo nucleophilic substitution with an amine $T_1T_2NH$, with $T_1$ and $T_2$ as defined previously, so as to give the nitrogenous compound (4) (scheme (1), pathway iii));
- or undergo nucleophilic substitution with an alkoxide $T_1T_2N$-L-O⁻, M⁺ with L, M⁺, $T_1$ and $T_2$ as defined previously, so as to give the intermediate (4) (scheme (2), pathway xiii)) so as to give the intermediate (3);
- or undergo nucleophilic substitution with an amine $T_1T_2NH$ with $T_1$ and $T_2$ as defined previously, so as to give the nitrogenous compound (5) (scheme (1), pathway v) and scheme (3), pathway xix));
- or undergo nucleophilic substitution with an amine $T_1T_2N$-L-N($T_3$)H with L and $T_1$ to $T_3$ as defined previously, so as to give the nitrogenous compound (6) (scheme (1), pathway vii));
- or undergo nucleophilic substitution with an amine Y-L-N($T_3$)H with Y, L and $T_1$ to $T_3$ as defined previously, so as to give the intermediate (7) which comprises a nucleofuge group Y (scheme (1), pathway ix)), it being possible for the latter to undergo nucleophilic substitution with an amine $T_1T_2NH$, with $T_1$ and $T_2$ as defined previously, so as to give the nitrogenous compound (6) (scheme (1), pathway x) and scheme (4), pathway xxv));

the intermediate (8) comprising a nucleofuge group $X'$ can then:

- either undergo nucleophilic substitution with an alkoxide $T_1T_2N$-L-O⁻, M⁺ with L, M⁺, $T_1$ and $T_2$ as defined previously, so as to give the intermediate (9) (scheme (2), pathway xiv));
- or undergo nucleophilic substitution with an amine $T_1T_2NH$ with $T_1$ and $T_2$ as defined previously, so as to give the nitrogenous compound (10) (scheme (3), pathway xx));
- or undergo nucleophilic substitution with an amine $T_1T_2N$-L-N($T_3$)H with L and $T_1$ to $T_3$ as defined previously, so as to give the nitrogenous compound (11) (scheme (4), pathway xxvi));
- or be reduced (scheme (2), pathway xii); scheme (3), pathway xviii); scheme (4), pathway xxiv)), by conventional reduction, preferably by hydroboration, such as $BH_3$, so as to give the compound (2) as defined previously;

the intermediates (9), (10), and (11) are then reduced by conventional reduction, preferably by hydroboration, such as with $BH_3$, so as to give the compounds (4), (5) and (6) respectively (scheme (2), pathway xv); scheme (3), pathway xxi); scheme (4), pathway xxvii));

the compounds (4), (5) or (6) are then reduced (scheme (1), pathways iv), vi) and vii); scheme (2), pathway xvi); scheme (3), pathway xxii), scheme (4), pathway xxviii)), by conventional reduction, preferably catalytic reduction, so as to give the compounds of formula (II), (III) or (IV) belonging to the compounds of formula (I):

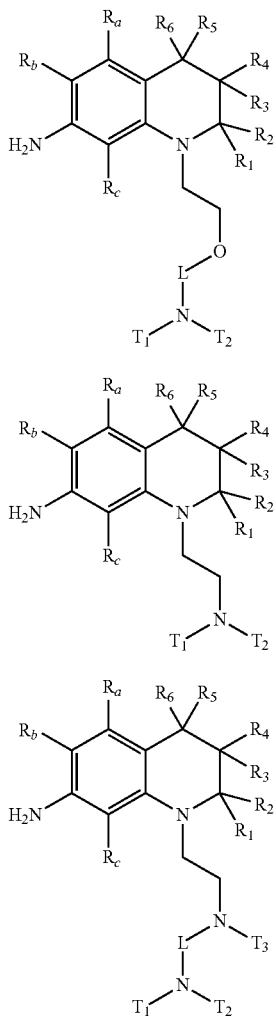

in which compounds (II), (III) and (IV), $R_a$ to $R_c$, $R_1$ to $R_6$, $T_1$ to $T_3$ and L are as defined previously.

The steps of reduction of the carbonyl, thiocarbonyl, or iminocarbonyl >C=W function of schemes (2), (3) and (4) are carried out under conventional conditions known to those skilled in the art; mention may be made of, for example, by hydroboration such as with $BH_3$ in a polar or non-polar solvent, for instance THF, glyme, dioxane or diethyl ether.

The reduction of the nitro group present in the final step of reaction schemes (1) to (4) is carried out under conventional conditions known to those skilled in the art, preferably by catalytic reduction, for example by performing a hydrogenation reaction under heterogeneous catalysis in the presence of Pd/C, Pd(II)/C, Ni/Ra, etc., or alternatively by performing a reduction reaction with a metal, for example with zinc, iron, tin, etc. (see *Advanced Organic Chemistry*, 3rd Edition, J. March, 1985, Wiley Interscience and *Reduction in Organic Chemistry*, M. Hudlicky, 1983, Ellis Horwood Series Chemical Science).

A subject of the invention is also the nitrogenous reaction intermediates (3), (4), (5), (6), (7), (8), (9), (10) and (11) as defined in schemes (1) to (4) above, with $R_a$ to $R_c$, $R_1$ to $R_6$, $T_1$ to $T_3$ and L as defined previously.

Composition

The present application also relates to a cosmetic dyeing composition, in particular for dyeing keratin fibres such as the hair, comprising, in a medium appropriate for dyeing, at least one 1,2,3,4-tetrahydroquinoline of general formula (I) as defined previously, with the exception of the compounds of formulae (A) to (C) as defined previously.

Preferably, the concentration of 1,2,3,4-tetrahydroquinoline of general formula (I) ranges from 0.0001% to 20% and preferably from 0.005% to 6% by weight relative to the total weight of the composition.

The medium appropriate for dyeing generally comprises water or a mixture of water and at least one organic solvent such as, for example, branched or unbranched $C_1$-$C_4$ lower alcohols, such as ethanol and isopropanol; polyols and polyol ethers, such as 2-butoxyethanol, propylene glycol, propylene glycol monomethyl ether, diethylene glycol monoethyl ether and monomethyl ether, and glycerol, and also aromatic alcohols such as benzyl alcohol or phenoxyethanol, and mixtures thereof.

Advantageously, the cosmetic composition comprises at least one cosmetic adjuvant chosen from the group made up of antioxidants, penetrants, sequestrants, fragrances, buffers, dispersants, surfactants, conditioning agents, film-forming agents, polymers, ceramides, preservatives, nacres or opacifiers, vitamins or provitamins.

The above adjuvants are generally present in an amount, for each of them, ranging from 0.01% to 20% by weight, relative to the weight of the composition.

The composition also comprises at least one oxidation base. These bases may in particular be chosen from para-phenylenediamines, bisphenylalkylenediamines, para-aminophenols, ortho-aminophenols and heterocyclic bases, and the addition salts thereof.

Among the para-phenylenediamines, mention may more particularly be made, by way of example, of para-phenylenediamine (PPD), para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl 3-methylaniline, N,N-bis-(β-hydroxyethyl)-para-phenylenediamine, 4-N,N-bis-(β-hydroxyethyl) amino-2-methylaniline, 4-N,N-bis-(β-hydroxyethyl)amino-2-chloroaniline, 2-3-hydroxyethyl-para-phenylenediamine, 2-fluoro-para-phenylenediamine, 2-isopropyl para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4' aminophenyl)pyrrolidine, 6-(4-aminophenylamino)hexan-1-ol, N-(4-amino-3-methylphenyl)-N-[3-(1H-imidazol-1-yl)propyl]amine, N-(4-aminophenyl)-N-[3-(1H-imidazol-1-yl)propyl]amine and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis-(β-hydroxyethyl)-para-phenylenediamine, 2-chloro-para-phenylenediamine, 2-β-acetylaminoethyloxy-para-phenylenediamine, 2-[{2-[(4-aminophenyl)amino]ethyl}(2-hydroxyethyl)amino]ethanol and the addition salts thereof with an acid are particularly preferred.

Among the bisphenylalkylenediamines, mention may be made, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols, mention may be made, by way of example, of para-aminophenol (PAP), 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6-[((5'-amino-2'-hydroxy-3'-methyl)phenyl)methyl]-2-methylphenol, bis[(5'-amino-2'-hydroxy)phenylmethane and the addition salts thereof with an acid.

Among the ortho-aminophenols, mention may be made, by way of example, of 2-aminophenol, 2-amino-5-methylphenol, 2-amino-6-methylphenol and 5-acetamido-2-aminophenol, and the addition salts thereof with an acid.

Among the heterocyclic bases, mention may be made, by way of example, of pyridine derivatives, pyrimidine derivatives and pyrazole derivatives.

The pyridine derivatives include the compounds described, for example, in patents GB 1 026 978 and GB 1 153 196, such as 2,5-diaminopyridine, 2-(4-methoxyphenyl)amino-3-aminopyridine, 3,4-diaminopyridine, and the addition salts thereof with an acid.

Other pyridine oxidation bases of use in the present invention are the 3-aminopyrazolo[1,5-a]pyridine oxidation bases or their addition salts described, for example, in patent application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and the addition salts thereof with an acid.

Among the pyridine bases that are of use in the present invention, mention may also be made of the compounds described in patent applications EP 1792903 and EP 1792606 and the addition salts thereof.

Mention may be made, among pyrimidine derivatives, of the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazolopyrimidine derivatives, mention may be made of the compounds described, for example, in patent applications EP 0847271, EP 0926149 and EP 1147109 and the addition salts thereof.

Among the pyrazole derivatives that may be mentioned are the compounds described in patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

By way of oxidation bases, mention may also be made of the diamino-N,N-dihydropyrazolone derivatives of formula (V) or one of the addition salts or solvates thereof:

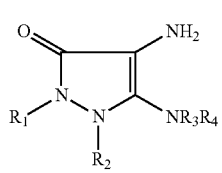

(V)

in which formula (V):

R$_1$, R$_2$, R$_3$ and R$_4$, which may be identical or different, represent:

a linear or branched C$_1$-C$_6$ alkyl radical optionally substituted with one or more radicals chosen from the group consisting of an —OR$_5$ radical, an —NR$_6$R$_7$ radical, a carboxy radical, a sulfonic radical, a carboxamido radical —C(O)—NR$_6$R$_7$, a sulfonamido radical —S(O)$_2$—NR$_6$R$_7$, a heteroaryl, an aryl optionally substituted with a (C$_1$-C$_4$)alkyl group, a hydroxyl, a C$_1$-C$_2$ alkoxy, an amino, or a (di)(C$_1$-C$_2$) alkylamino;

an aryl radical optionally substituted with one or more (C$_1$-C$_4$)alkyl, hydroxyl, C$_1$-C$_2$ alkoxy, amino or (di)(C$_1$-C$_2$)alkylamino;

a 5- or 6-membered heteroaryl radical, optionally substituted with one or more radicals chosen from (C$_1$-C$_4$)alkyl and (C$_1$-C$_2$)alkoxy;

R$_3$ and R$_4$ may also represent a hydrogen atom;

R$_5$, R$_6$ and R$_7$, which may be identical or different, represent a hydrogen atom; a linear or branched C$_1$-C$_4$ alkyl radical optionally substituted with one or more radicals chosen from the group consisting of a hydroxyl, a $C_1$-$C_2$ alkoxy, a carboxamido —C(O)—$NR_8R_9$, a sulfonyl —$S(O)_2$—$R_8$, an aryl optionally substituted with a ($C_1$-$C_4$)alkyl, a hydroxyl, a $C_1$-$C_2$ alkoxy, an amino, a (di)($C_1$-$C_2$)alkylamino; an aryl optionally substituted with a ($C_1$-$C_4$)alkyl, a hydroxyl, a $C_1$-$C_2$ alkoxy, an amino, or a (di)($C_1$-$C_2$)alkylamino;

$R_6$ and $R_7$, which may be identical or different, may also represent a carboxamido radical —C(O)—$NR_8R_9$; a sulfonyl —$S(O)_2$—$R_8$;

$R_8$ and $R_9$, which may be identical or different, represent a hydrogen atom; or a linear or branched $C_1$-$C_4$ alkyl radical which is optionally substituted with one or more of hydroxyl or $C_1$-$C_2$ alkoxy;

$R_1$ and $R_2$, on the one hand, and $R_3$ and $R_4$, on the other hand, may form, with the nitrogen atoms to which they are attached, a saturated or unsaturated heterocycle containing 5 to 7 members which is optionally substituted with one or more radicals chosen from the group consisting of halogen atoms, amino, (di)($C_1$-$C_4$)alkylamino, hydroxyl, carboxyl, carboxamido and ($C_1$-$C_2$) alkoxy radicals, and $C_1$-$C_4$ alkyl radicals optionally substituted with one or more hydroxyl, amino, (di)alkylamino, alkoxy, carboxyl or sulfonyl radicals;

$R_3$ and $R_4$ may also form, together with the nitrogen atom to which they are attached, a 5- or 7-membered heterocycle in which the carbon atoms may be replaced with an optionally substituted oxygen or nitrogen atom.

These diamino-N,N-dihydropyrazolone derivatives are described in particular in application FR 2866338, and one particularly preferred derivative is 2,3-diamino-6,7-dihydro-1H,5H-pyrazolo[1,2-a]pyrazol-1-one dimethanesulfonate.

Oxidation bases that may also be mentioned include the diamino-N,N-dihydropyrazolone derivatives of formula (VI) or one of the addition salts or solvates thereof:

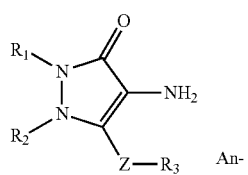

(VI)

in which formula (VI):

Z represents independently:
  a covalent single bond,
  a divalent radical chosen from an oxygen atom and an —N($R_6$)— radical, with $R_6$ representing a hydrogen atom or a $C_1$-$C_6$ alkyl radical, or $R_6$ with $R_3$ together form, with the nitrogen atom which bears them, a substituted or unsubstituted, saturated or unsaturated and aromatic 5- to 8-membered heterocycle, optionally containing one or more other heteroatoms or groups chosen from N, O, S, —$S(O)_2$—, and —C(O)—, it being possible for the heterocycle to be cationic and/or substituted with a cationic radical,
  a divalent radical —$N^+(R_7)(R_8)$— with $R_7$ and $R_8$ independently representing a $C_1$-$C_6$ alkyl radical; the alkyl radical may be substituted with an OH or an alkoxy: —O($C_1$-$C_6$)alkyl, $R_3$ represents:
  a hydrogen
  a $C_1$-$C_{10}$ alkyl radical which is optionally substituted, it being possible for the alkyl radical to be interrupted with a heteroatom or a group chosen from O, N, Si, S, —S(O)— and —$S(O)_2$—,
  a $C_1$-$C_{10}$ alkyl radical which is substituted and/or interrupted with a cationic radical,
  a halogen,
  an —$SO_3H$ radical,
  a 5- to 8-membered ring which is substituted or unsubstituted, saturated, unsaturated or aromatic, optionally containing one or more heteroatoms or groups chosen from N, O, S, —$S(O)_2$— and —O(O)—, it being possible for the ring to be cationic and/or substituted with a cationic radical, $R_1$ and $R_2$, which may be identical or different, represent:
  a linear or branched $C_1$-$C_6$ alkyl radical optionally substituted with one or more radicals chosen from an $OR_5$ radical, an —$NR_9R_{10}$ radical, a carboxy radical, a sulfonic radical, a carboxamido radical —C(O)—$NR_9R_{10}$, a sulfonamido radical —$S(O)_2$—$NR_9R_{10}$, a heteroaryl, an aryl optionally substituted with a ($C_1$-$C_4$)alkyl group, a hydroxyl group, a $C_1$-$C_2$ alkoxy group, an amino group, or a (di)($C_1$-$C_2$)alkylamino group;
  an aryl radical optionally substituted with one or more ($C_1$-$C_4$)alkyl, hydroxyl, $C_1$-$C_2$ alkoxy, amino or (di)($C_1$-$C_2$)alkylamino;
  a 5- or 6-membered heteroaryl radical which is optionally substituted with one or more radicals chosen from ($C_1$-$C_4$)alkyl which is monosubstituted or polysubstituted with the radical an OH or an —Oalkyl, or ($C_1$-$C_2$)alkoxy;

$R_1$ and $R_2$ may form, with the nitrogen atoms to which they are attached, a saturated or unsaturated heterocycle containing 5 to 7 members which is optionally substituted with one or more radicals chosen from the group consisting of halogen atoms, amino, (di)($C_1$-$C_4$)alkylamino, hydroxyl, carboxyl, carboxamido and ($C_1$-$C_2$)alkoxy radicals, and $C_1$-$C_4$ alkyl radicals which are optionally substituted with one or more hydroxyl, amino, (di)alkylamino, alkoxy, carboxyl or sulfonyl radicals, An— represents an anion or a group of anions making it possible to ensure the electroneutrality of the compounds of formula (VI), on the condition that at least one of the groups Z and $R_3$ represents a cationic radical. These derivatives of diamino-N,N-dihydropyrazolone are described in patent application FR 2 927 078.

In general the concentration of the oxidation base(s) ranges from 0.0001% to 20% and preferably from 0.005% to 6% by weight, relative to the total weight of the composition.

The composition according to the invention preferably comprises at least one additional oxidation coupler other than the 1,2,3,4-tetrahydroquinolines of general formula (I).

Among these oxidation couplers, mention may in particular be made of meta-phenylenediamines, meta-aminophenols, meta-diphenols, naphthalenic couplers and heterocyclic couplers, and the addition salts thereof.

By way of example, mention may be made of 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3- diaminobenzene, 1,3-bis-(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene and the addition salts thereof.

In general, the concentration of the oxidation coupler(s) ranges from 0.0001% to 20% and preferably from 0.005% to 6% by weight, relative to the total weight of the composition.

In general, the addition salts with an acid that can be used for the oxidation bases and the couplers are chosen in particular from hydrochlorides, hydrobromides, sulfates, citrates, succinates, tartrates, lactates, tosylates, benzenesulfonates, phosphates and acetates.

Preferably the oxidation base is chosen from the paraphenylene-diamines such as PPD, and para-aminophenols such as PAP.

The dyeing composition in accordance with the invention may further comprise one or more direct dyes, which may in particular be chosen from neutral, acidic or cationic nitrobenzene dyes, neutral, acidic or cationic azo direct dyes, neutral, acidic or cationic quinone, and especially anthraquinone, direct dyes, azine direct dyes, methine, azomethine, triarylmethane and indoamine direct dyes and natural direct dyes. The composition according to the invention preferably comprises at least one dye selected from cationic direct dyes and natural direct dyes.

Among the cationic direct dyes that can be used according to the invention, mention may be made of the cationic azo direct dyes described in patent applications WO 95/15144, WO 95/01772 and EP-714954.

Among these compounds, mention may be made very particularly of the following dyes:
- 1,3-dimethyl-2-[[4-(dimethylamino)phenyl]azo]-1H-imidazolium halide (chloride),
- 1,3-dimethyl-2-[(4-aminophenyl)azo]-1H-imidazolium halide (chloride),
- 1-methyl-4-[(methylphenylhydrazono)methyl]pyridinium salt (methyl sulfate).

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes and in particular henna-based extracts or poultices may also be used.

The direct dye or dyes represents or represent, preferably, from 0.001% to 20% by weight, approximately, of the total weight of the composition, and even more preferably approximately from 0.005% to 10% by weight.

Those skilled in the art will of course ensure that the adjuvant(s), additional oxidation dye precursors and direct dyes are chosen such that the advantageous properties intrinsically attached to the oxidation dyeing composition in accordance with the invention are not, or not substantially, adversely affected by the intended addition(s).

The pH of the dyeing composition in accordance with the invention is generally between approximately 3 and 12 and preferably between approximately 5 and 11. It may be adjusted to the desired value by means of acidifying or alkalinizing agents customarily used in the dyeing of keratin fibres, or alternatively using standard buffer systems.

Among the acidifying agents, mention may be made of those already mentioned for salifying the compounds of formula (I) to give a salt of an organic or inorganic acid, by way of example, inorganic or organic acids other than dicarboxylic acids, such as hydrochloric acid, ortho-phosphoric acid, sulfuric acid, carboxylic acids such as acetic acid, tartaric acid, citric acid or lactic acid, and sulfonic acids.

Among the alkalinizing agents, mention may be made of those already mentioned for salifying the compound of formula (I) to give a salt of an organic or inorganic base, by way of example, aqueous ammonia, alkali metal carbonates, alkanolamines, such as mono-, di- and triethanolamines, and derivatives thereof, sodium hydroxide, potassium hydroxide and the compounds of formula (VII):

(VII)

in which formula (VII), G is a linear or branched ($C_1$-$C_6$) alkylene group, optionally interrupted with one or more heteroatoms such as O or N, and/or optionally substituted with a hydroxyl group, particularly G represents a propylene group; $R^a$, $R^b$, $R^c$ and $R^d$, which may be identical or different, represent a hydrogen atom, or a $C_1$-$C_4$ alkyl or $C_1$-$C_4$ hydroxyalkyl radical.

The cosmetic composition according to the invention may be present in a variety of forms, such as in the form of liquids, creams, gels, or any other form which is appropriate for carrying out dyeing of keratin fibres, and in particular of human hair.

A subject of the present application is also a process for dyeing keratin fibres, in which the composition is applied to said fibres for a time sufficient to develop the desired coloration in the presence of an oxidizing agent, the oxidizing agent being applied before, simultaneously with or after the composition.

The colour may be developed at acidic, neutral or alkaline pH, and the oxidizing agent may be added to the composition of the invention just at the time of use, or it may be used starting from an oxidizing composition which comprises it and which is applied simultaneously with or sequentially to the composition of the invention.

In one particular embodiment, the composition according to the present invention is mixed, preferably at the time of use, with a composition containing, in a medium appropriate for dyeing, at least one oxidizing agent, this oxidizing agent being present in an amount sufficient to develop a coloration.

In this particular embodiment, a ready-to-use composition is available which is a mixture of a composition according to the invention with at least one oxidizing agent. The resulting mixture is subsequently applied to the keratin fibres for a time sufficient for the desired coloration to develop. After a leave-in time of approximately 3 to 50 minutes, preferably approximately 5 to 30 minutes, the keratin fibres are rinsed, washed with shampoo, rinsed again and then dried.

The oxidizing agents conventionally used for the oxidation dyeing of keratin fibres are, for example, hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

The oxidizing composition may also contain various adjuvants conventionally used in compositions for dyeing the hair and as defined previously.

The pH of the oxidizing composition containing the oxidizing agent is such that, after mixing with the dyeing composition, the pH of the resulting composition applied to the keratin fibres preferably ranges between 3 and 12 approximately and even more preferentially between 5 and 11. It may be adjusted to the desired value by means of acidifying or alkalinizing agents customarily used in the dyeing of keratin fibres and as defined above.

The ready-to-use composition which is ultimately applied to the keratin fibres may be in a variety of forms, such as in the form of liquids, creams or gels or any other form appropriate for carrying out dyeing of keratin fibres, and in particular of human hair.

The present application further provides a method of dyeing keratin fibres, in which the ready-to-use composition is applied to said fibres for a time sufficient to develop the desired coloration.

The time sufficient to develop the desired coloration corresponds in general to a leave-in time of approximately 3 to 50 minutes, preferably approximately 5 to 30 minutes.

The invention further provides a multi-compartment device or dyeing kit in which a first compartment contains the dyeing composition defined above and a second compartment contains an oxidizing composition. This device may be equipped with a means allowing the desired mixture to be delivered to the hair, such as the devices described in patent FR-2 586 913 in the name of the Applicant.

Using this device, it is possible to dye the keratin fibres on the basis of a process which comprises mixing a dyeing composition in accordance with the invention with an oxidizing agent as defined previously, and applying the resulting mixture to the keratin fibres for a time sufficient to develop the desired coloration.

The evaluation of the coloration can be done visually or read on a spectrocolorimeter (such as Minolta CM3600d, illuminant D65, angle 10°, SCI values) for the L*, a*, b* colorimetric measurements. In this L*, a*, b* system, L* represents the intensity of the color, a* indicates the green/red color axis and b* indicates the blue/yellow color axis.

The lower the value of L, the darker or more intense the color.

The higher the value of a*, the redder the shade; the higher the value of b*, the yellower the shade.

The variation in coloring between the colored locks of natural white hair which is untreated (control) and after treatment or coloration are defined by $\Delta E^*$, corresponding to the colour uptake on keratin fibers, according to the following equation:

$$\Delta E^* = \sqrt{(L^* - L_0^*)^2 + (a^* - a_0^*)^2 + (b^* - b_0^*)^2}$$

In this equation, L*, a* and b* represent the values measured after dyeing the natural hair comprising 90% of white hairs and $L_0^*$, $a_0^*$ and $b_0^*$ represent the values measured for the untreated natural hair comprising 90% of white hairs.

The greater the value of $\Delta E$, the greater the difference in color between the control locks and the dyed locks and the greater colour uptake is.

Chromaticity in the CIE L*, a*, b* colorimetric system is calculated according to the following equation:

$$C^* = \sqrt{a^{*2} + b^{*2}}$$

The greater the value of C*, the greater the chromaticity is.

The examples that follow serve to illustrate the invention without, however, being limiting in nature.

EXAMPLES a) Synthesis of 1-(chloroacetyl)-7-nitro-1,2,3,4-tetrahydroquinoline

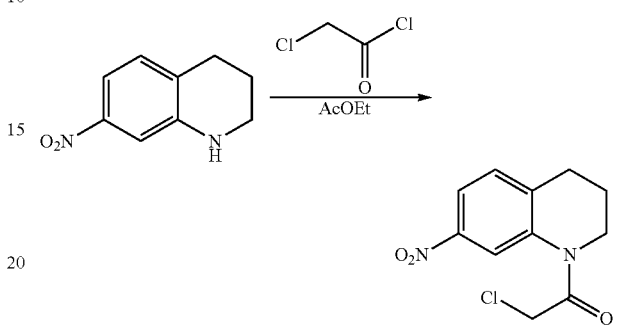

1.78 g of 7-nitro-1,2,3,4-tetrahydroquinoline (0.01 mol) are dissolved in 15 ml of ethyl acetate. This solution is run into a mixture of 15 ml of ethyl acetate and 0.80 ml of chloroacetyl chloride. A white precipitate forms immediately, and stirring is continued at 30° C. for 2 h (the reaction is monitored by thin layer chromatography (90/10 ethyl acetate/heptane)). After 2 h, since the reaction is incomplete, 0.2 equivalent of chloroacetyl chloride is added and the temperature is raised to 60° C.; the solid formed undergoes dissolution. When the reaction has finished, the medium is cooled and the solvent is evaporated off. 2.46 g of a beige product which corresponds to the expected compound are recovered.

The spectroscopic and spectrometric data are in accordance with the structure of the expected compound.

Example 1

1-[2-(1H-imidazol-1-yl)ethyl]-1,2,3,4-tetrahydroquinolin-7-amine dihydrochlorides

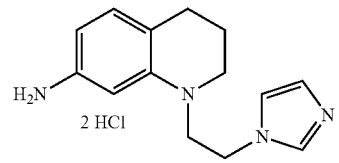 [SMILES: Nc1ccc2c(c1)N(CCn1ccnc1)CCC2]

b) Synthesis of 2-(1H-imidazol-1-yl)-1-(7-nitro-3,4-dihydroquinolin-1(2H)-yl)ethanone

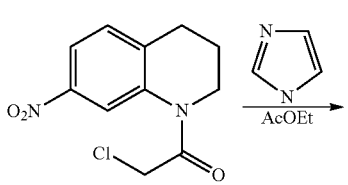

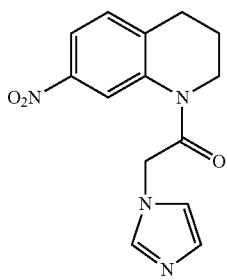

2 g of 1-(chloroacetyl)-7-nitro-1,2,3,4-tetrahydroquinoline (0.008 mol) are solubilized in 30 ml of hot ethyl acetate (40° C.), and 1.088 g of imidazole (0.016 mol) are added. The medium is taken to reflux, and the formation of a white precipitate is observed. The reaction is monitored by TLC (90/10 ethyl acetate/heptane) and mass spectrometry. When the starting product is no longer detected by mass spectrometry, the precipitate formed is filtered off hot on a frit, and then washed with ethyl acetate and isopropyl ether, before being dried under vacuum.

A pale yellow solid corresponding to the expected compound is thus isolated.

The spectroscopic and spectrometric data are in accordance with the structure of the expected compound.

c) Synthesis of 1-[2-(1H-imidazol-1-yl)ethyl]-7-nitro-1,2,3,4-tetrahydroquinoline

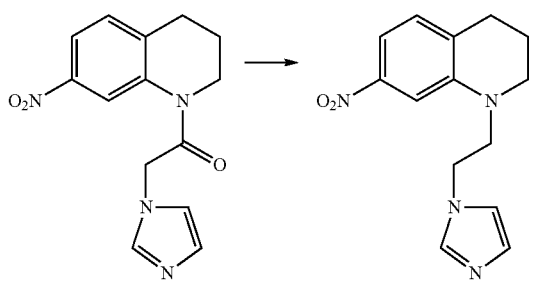 [SMILES: O=C(Cn1ccnc1)N1CCCc2ccc([N+](=O)[O-])cc21 ; O=[N+]([O-])c1ccc2c(c1)N(CCn1ccnc1)CCC2]

In a 100-ml round-bottomed, three-necked flask fitted with a condenser and a thermometer, under an inert (nitrogen) atmosphere, 8.6 g (30 mmol) of 2-(1H-imidazol-1-yl)-1-(7-nitro-3,4-dihydroquinolin-1-(2H)-yl)ethanone are dissolved in 10 ml of dry THF. The solution was stirred at 0° C. and 150 ml (5 eq) of a 1.0M solution of BH$_3$ in THF were added. The reaction medium was left to return to ambient temperature and was then stirred overnight. The reaction mixture was carefully acidified (drop by drop) with 1N HCl (considerable foaming and release of gas), before being brought to reflux for 0.5 h. The mixture was then cooled to ambient temperature and neutralized with 4.0N sodium hydroxide. The medium is extracted several times with ethyl acetate. The organic phases were combined, and dried over MgSO$_4$. After filtration, the solvent was removed by evaporation. The residue was purified by chromatography on a column of silica (dichloromethane/methanol). After evaporation of the solvents, crystallization was initiated with diethyl ether so as to give the expected product: 1-(2-(1H-imidazol-1-yl)ethyl)-7-nitro-1,2,3,4-tetrahydroquinoline in the form of an orange solid (Mp 120-121° C.).

The spectroscopic and spectrometric data are in accordance with the structure of the expected compound.

d) Synthesis of 1-[2-(1H-imidazol-1-yl)ethyl]-1,2,3,4-tetrahydroquinolin-7-amine dihydrochloride

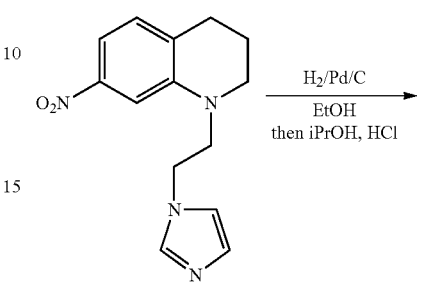

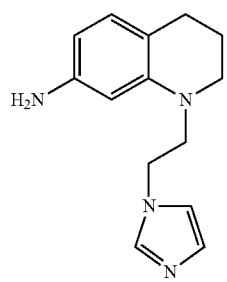

The reduction step is carried out by means of a hydrogenation system using a solution of 5 g (3.85 mmol) of 1-[2-(1H-imidazol-1-yl)ethyl]-7-nitro-1,2,3,4-tetrahydroquinoline in 78.5 ml of ethanol which is introduced into the system equipped with a 90×4 mm cartridge of Pd/C 10%-type catalyst.

The reduction is carried out under the following conditions: pump flow rate 5 ml/min, temperature 75° C., pressure 70 bar and under a hydrogen flow rate of 125 ml/min.

On leaving the hydrogenation system, the reduced product is trapped in 20 ml of iPrOH/6.0N HCl so as to form the dihydrochloride, and the solvent is then removed by evaporation under vacuum until a white solid is obtained. The latter is taken up with 30 ml of diisopropyl ether, dried by suction in the presence of argon, and then dried under vacuum at 45° C. in a desiccator in the presence of a drying agent until a constant weight is obtained. 1.13 g of white solid corresponding to the expected compound are thus isolated.

The spectroscopic and spectrometric data are in accordance with the structure of the expected compound.

Example 2

1-[2-(dimethylamino)ethyl]-1,2,3,4-tetrahydroquinolin-7-amine

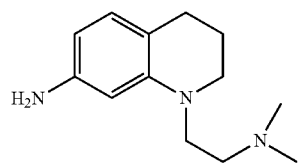 [SMILES: CN(C)CCN1CCCc2ccc(N)cc21]

e) Synthesis of 2-(dimethylamino-1-(7-nitro-3,4-dihydroquinolin-1(2H)-yl)ethanone

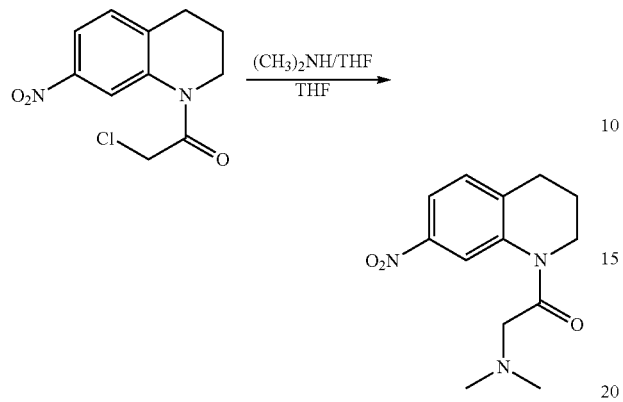

2-chloro-1-(7-nitro-3,4-dihydroquinolin-1(2H)-yl)ethanone (1 g, 3.9 mmol) was dissolved in 10 ml of dry THF and 7.8 ml of a 1M solution of dimethylamine in THF (7.8 mmol) were added. This reaction mixture was stirred at ambient temperature for 24 h. The solvent was removed under reduced pressure and the residue was crystallized from diethyl ether to give the expected compound 2-(dimethylamino)-1-(7-nitro-3,4-dihydroquinolin-1(2H)-yl)ethanone in the form of a brown solid (Mp 130-132° C.).

The spectroscopic and spectrometric data are in accordance with the structure of the expected compound.

f) Synthesis of N,N-Dimethyl-2-(7-nitro-3,4-dihydroquinolin-1(2H)-yl)ethanamine

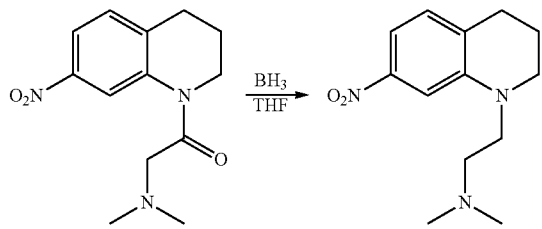

Under a nitrogen atmosphere, 1.2 g (4.6 mmol) of 2-(dimethylamino)-1-(7-nitro-3,4-dihydroquinolin-1(2H)-yl)ethanone were dissolved in 20 ml of dry THF. The solution was stirred at 0° C. and 25 ml of a 1.0M solution of $BH_3$ in THF were added. The temperature is left to return to ambient temperature and the reaction mixture is left stirring at ambient temperature for 5 h. The reaction mixture was carefully (drop by drop) acidified with 5 ml of 3N HCl (vigorous foaming and release of gas) and then brought to reflux for 0.5 h. After cooling to ambient temperature, the medium is alkalinized with a 1.0N aqueous solution of NaOH. The medium is then extracted several times with ethyl acetate. The organic phases were combined, and dried over $Na_2SO_4$. After filtration, the solvent was removed by evaporation. Addition of a small amount of diethyl ether resulted in crystallization.

The solid form was dried by suction and, after drying under vacuum in the presence of a drying agent until a constant weight was obtained, the expected N,N-dimethyl-2-(7-nitro-3,4-dihydroquinolin-1(2H)-yl)ethanamine was isolated in the form of an orange powder (Mp 126-128° C.).

The spectroscopic and spectrometric data are in accordance with the structure of the expected compound.

g) Synthesis of 1-[2-(dimethylamino)ethyl]-1,2,3,4-tetrahydroquinolin-7-amine dihydrochloride

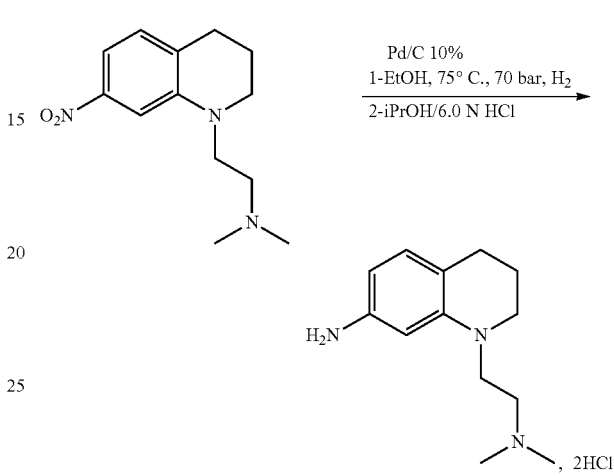

The reduction step is carried out using a hydrogenation system. A solution of 1.24 g (49.8 mmol) of N,N-dimethyl-2-(7-nitro-3,4-dihydroquinolin-1(2H)-yl)ethanamine in 78.5 ml of ethanol is introduced into a system equipped with a 90×4 mm cartridge of Pd/C 10%-type catalyst.

The reduction is carried out under the following conditions: pump flow rate 1.4 ml/min, temperature 80° C., pressure 70 bar and under a hydrogen flow rate of 125 ml/min.

On leaving the system, the reduced product is trapped in 100 ml of iPrOH/6.0N HCl so as to form the hydrochloride, and the solvent is then removed by evaporation under vacuum until a white solid is obtained. The latter is taken up with 30 ml of diisopropyl ether, dried by suction under an argon atmosphere, and then dried under vacuum at 45° C. in a desiccator in the presence of a drying agent until a constant weight is obtained. The product isolated is in the form of a beige solid, corresponding to the expected compound.

The spectroscopic and spectrometric data are in accordance with the structure of the expected compound.

Example 3

1-[2-(4-methylpiperazin-1-yl)ethyl]-1,2,3,4-tetrahydroquinolin-7-amine dihydrochloride

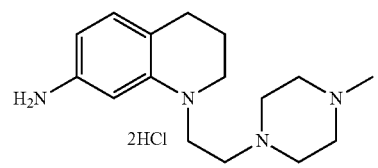 [SMILES: CN1CCN(CCN2CCCc3ccc(N)cc32)CC1]

h) Synthesis of 2-(4-methylpiperazin-1-yl)-1-(7-nitro-3,4-dihydroquinolin-1 (2H)-yl)ethanone

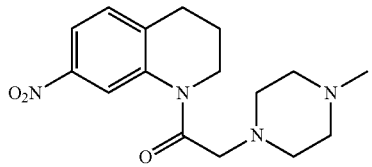 [SMILES: CN1CCN(CC(=O)N2CCCc3ccc([N+](=O)[O-])cc32)CC1]

2-Chloro-1-(7-nitro-3,4-dihydroquinolin-1(2H)-yl)ethanone (1 g, 3.9 mmol) was dissolved in dry THF (10 ml) and 0.8 g (7.8 mmol) of N-methylpiperazine was added. The reaction mixture was stirred at ambient temperature for 6 hours. The product obtained precipitates from the medium, it is dried by suction and washed with diethyl ether.

After drying under vacuum in the presence of a drying agent until a constant weight is obtained, the expected 2-(4-methylpiperazin-1-yl)-1-(7-nitro-3,4-dihydroquinolin-1 (2H)-yl)ethanone is isolated in the form of a brown solid (Mp 142-144° C.).

The spectroscopic and spectrometric data are in accordance with the structure of the expected compound.

i) Synthesis of 1-(2-(4-methylpiperazin-1-yl)ethyl)-7-nitro-1,2,3,4-tetrahydroquinoline

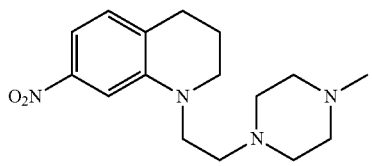 [SMILES: CN1CCN(CCN2CCCc3ccc([N+](=O)[O-])cc32)CC1]

Under a nitrogen atmosphere, 6 g (18 mmol) of 2-(4-methylpiperazin-1-yl)-1-(7-nitro-3,4-dihydroquinolin-1 (2H)-yl)ethanone are dissolved in 20 ml of anhydrous THF. With stirring, at 0° C., a solution of 100 ml of 1.0M $BH_3$ in THF (5.5 eq) is added. The temperature was allowed to return to ambient temperature and stirring was carried out for 24 h, before acidifying (drop by drop) with 1N HCl (considerable foaming and release of gas), and the medium was then brought to reflux for 0.5 h. After a return to ambient temperature, a 4.0N aqueous solution of NaOH was added. The medium was extracted several times with ethyl acetate. The combined organic phases were dried over $Na_2SO_4$, and then filtered. After removal of the solvent, a residue was obtained, which was purified on a silica column (dichloromethane-methanol). 1-(2-(4-Methylpiperazin-1-yl)ethyl)-7-nitro-1,2,3,4-tetrahydroquinoline was thus obtained in the form of an orange powder (Mp 58-60° C.).

The spectroscopic and spectrometric data are in accordance with the structure of the expected compound.

j) Synthesis of 1-[2-(4-methylpiperazin-1-yl)ethyl]-1,2,3,4-tetrahydroquinolin-7-amine dihydrochloride

The reduction step is carried out using a hydrogenation system. A solution of 2.10 g (6.89 mmol) of 1-(2-(4-methylpiperazin-1-yl)ethyl)-7-nitro-1,2,3,4-tetrahydroquinoline in 78.5 ml of ethanol is introduced into the system equipped with a 90×4 mm cartridge of Pd/C 10%-type catalyst.

The reduction is carried out under the following conditions: pump flow rate 1.4 ml/min, temperature 80° C., pressure 70 bar and under a hydrogen flow rate of 125 ml/min.

On leaving the system, the reduced product is trapped in 100 ml of iPrOH/6.0N HCl so as to form the hydrochloride, and the solvent is then removed by evaporation under vacuum until a white solid is obtained. The latter is taken up with 30 ml of diisopropyl ether, dried by suction under an inert (argon) atmosphere, and then dried under vacuum at 45° C. in a desiccator in the presence of a drying agent until a constant weight is obtained. A white solid corresponding to the expected compound was isolated.

The spectroscopic and spectrometric data are in accordance with the structure of the expected compound.

Examples of Dyeing

The following dyeing compositions are prepared:

| Example 3 | | | |
|---|---|---|---|
| 1-[2-(1H-imidazol-1-yl)ethyl]-1,2,3,4-tetrahydroquinolin-7-amine dihydrochlorides (example 1) | $10^{-3}$ mol | $10^{-3}$ mol | $10^{-3}$ mol |
| 2,3-diamino-6,7-dihydro-1H,5H-pyrazolo[1,2-a]pyrazol-1-one dimethanesulfonate | $10^{-3}$ mol | | |
| 2-[(3-aminopyrazolo[1,5-a]pyrid-2-yl)oxy]ethanol hydrochloride | | $10^{-3}$ mol | |
| 4-(3-aminopyrazolo[1,5-a]pyrid-2-yl)-1,1-dimethylpiperazin-1-ium chloride hydrochloride | | | $10^{-3}$ mol |
| Dye support (1) | (*) | (*) | (*) |
| Demineralized water qs | 100 g | 100 g | 100 g |
| Shade observed | strong crimson red | strong violet | strong blue-green |

| Example 2 | | | |
|---|---|---|---|
| 1-[2-(dimethylamino)ethyl]-1,2,3,4-tetrahydroquinolin-7-amine (example 2) | $10^{-3}$ mol | $10^{-3}$ mol | $10^{-3}$ mol |
| 2,3-diamino-6,7-dihydro-1H,5H-pyrazolo[1,2-a]pyrazol-1-one dimethanesulfonate | $10^{-3}$ mol | | |
| 2-[(3-aminopyrazolo[1,5-a]pyrid-2-yl)oxy]ethanol hydrochloride | | $10^{-3}$ mol | |
| 4-(3-aminopyrazolo[1,5-a]pyrid-2-yl)-1,1-dimethylpiperazin-1-ium chloride hydrochloride | | | $10^{-3}$ mol |

Example 2

| Dye support (1) | (*) | (*) | (*) |
|---|---|---|---|
| Demineralized water qs | 100 g | 100 g | 100 g |
| Shade observed | strong crimson red | chromatic strong violet | chromatic strong blue-green |

Example 3

| | | | |
|---|---|---|---|
| 1-[2-(dimethylamino)ethyl]-1,2,3,4-tetrahydroquinolin-7-amine (example 3) | $10^{-3}$ mol | $10^{-3}$ mol | $10^{-3}$ mol |
| 2,3-diamino-6,7-dihydro-1H,5H-pyrazolo[1,2-a]pyrazol-1-one dimethanesulfonate | $10^{-3}$ mol | | |
| 2-[(3-aminopyrazolo[1,5-a]pyrid-2-yl)oxy]ethanol hydrochloride | | $10^{-3}$ mol | |
| 4-(3-aminopyrazolo[1,5-a]pyrid-2-yl)-1,1-dimethylpiperazin-1-ium chloride hydrochloride | | | $10^{-3}$ mol |
| Dye support (1) | (*) | (*) | (*) |
| Demineralized water qs | 100 g | 100 g | 100 g |
| Shade observed | strong coppery red | chromatic strong violet | chromatic strong blue-green |

(*): dye support (1) pH = 9.5

Dye Support:

| | |
|---|---|
| 96° ethyl alcohol | 20.8 g |
| 35% aqueous sodium metabisulfite solution | 0.23 g AM |
| Pentasodium salt of diethylenetriaminepentaacetic acid as an aqueous 40% solution | 0.48 g AM |
| $C_8$-$C_{10}$ alkyl polyglucoside as an aqueous 60% solution | 3.6 g AM |
| Benzyl alcohol | 2.0 g |
| Polyethylene glycol containing 8 units of ethylene oxide | 3.0 g |
| $NH_4Cl$ | 4.32 g |
| Aqueous ammonia containing 20% $NH_3$ | 2.94 g |

At the time of use, each composition is mixed with an equal weight of 20-volumes aqueous hydrogen peroxide solution (6% by weight). A final pH of 9.5 is obtained.

Each mixture obtained is applied to locks of grey hair containing 90% white hairs. After a leave-in time of 30 minutes, the locks are rinsed, washed with a standard shampoo, rinsed again and then dried.

Comparative Examples of Dyeing

| ingredients | Composition 1 (Comparative) | Composition 2 (Invention) |
|---|---|---|
| para aminophenol (PAP) | $10^{-3}$ mol | $10^{-3}$ mol |
| 1,2,3,4-tetrahydroquinolin-7-amine | $10^{-3}$ mol | |
| 1[2-(dimethylamino)ethyl]-1,2,3,4-tetrahydroquinolin-7-amine hydrochloride | | $10^{-3}$ mol |
| Dye support (1) | (*) | (*) |
| Demineralized water qs | 100 g | 100 g |

| ingredients | Composition 3 (Comparative) | Composition 4 (Invention) |
|---|---|---|
| 4-aminophenylamine dihydrochloride (PPD) | $10^{-3}$ mol | $10^{-3}$ mol |
| 1,2,3,4-tetrahydroquinolin-7-amine | $10^{-3}$ mol | |
| 1[2-(dimethylamino)ethyl]-1,2,3,4-tetrahydroquinolin-7-amine hydrochloride | | $10^{-3}$ mol |
| 4-(3-aminopyrazolo[1,5-a]pyrid-2-yl)-1,1-dimethylpiperazin-1-ium chloride hydrochloride | | |
| Dye support (1) | (*) | (*) |
| Demineralized water qs | 100 g | 100 g |

(*): dye support (1) pH = 9.5

Dye Support:

| | |
|---|---|
| 96° ethyl alcohol | 20.8 g |
| 35% aqueous sodium metabisulfite solution | 0.23 g AM |
| Pentasodium salt of diethylenetriaminepentaacetic acid as an aqueous 40% solution | 0.48 g AM |
| $C_8$-$C_{10}$ alkyl polyglucoside as an aqueous 60% solution | 3.6 g AM |
| Benzyl alcohol | 2.0 g |
| Polyethylene glycol containing 8 units of ethylene oxide | 3.0 g |
| $NH_4Cl$ | 4.32 g |
| Aqueous ammonia containing 20% $NH_3$ | 2.94 g |

At the time of use, each composition is mixed with an equal weight of 20-volumes aqueous hydrogen peroxide solution (6% by weight). A final pH of 9.5 is obtained.

Each mixture obtained is applied to locks of grey hair containing 90% white hairs. After a leave-in time of 30 minutes, the locks are rinsed, washed with a standard shampoo, rinsed again and then dried.

Colorimetric Evaluation:

The evaluation of the coloration is done visually and read on a spectrocolorimeter (such as Minolta CM3600d, illuminant D65, angle 10°, SCI values) for the L*, a*, b* colorimetric measurements. In this L*, a*, b* system, L* represents the intensity of the color, a* indicates the green/red color axis and b* indicates the blue/yellow color axis.

The lower the value of L, the darker or more intense the color.

The higher the value of a*, the redder the shade; the higher the value of b*, the yellower the shade.

Chromaticity in the CIE L*, a*, b* colorimetric system is calculated according to the following equation:

$$C^* = \sqrt{a^{*2} + b^{*2}}$$

The greater the value of C*, the greater the chromaticity is.

| Chromaticity | Composition 1 (Comparative) | Composition 2 (Invention) |
|---|---|---|
| C* moyen | 6.32 (composition 1) | 15.10 (composition 2) |
| C* moyen | 5.33 (composition 3) | 7.57 (composition 3) |

As it can be observed from the table, the keratin fibers treated with composition according to the invention give a significantly more chromatic colour than the ones according to the comparative composition.

The invention claimed is:

1. A method for dyeing keratin fibers comprising applying a cosmetic composition to said keratin fibers, said composition comprising:
   at least one heterocyclic coupler chosen from compounds of formula (I), salts thereof, optical or geometric isomers thereof, or solvates thereof:

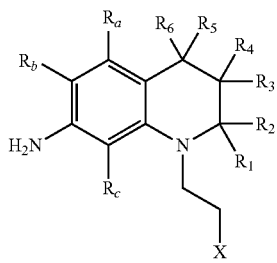

(I)

wherein:
R₁, R₂, R₃, R₄, R₅ and R₆ are independently chosen from:
i) hydrogen or halogen atoms;
ii) linear or branched $C_1$-$C_6$ alkyl radicals, optionally substituted with one or more hydroxyl groups;
iii) ($C_1$-$C_6$)alkoxycarbonyl radicals —C(O)—O—R, wherein R represents a linear or branched $C_1$-$C_6$ alkyl radical; and
iv) alkylcarbonyloxy radicals —O—C(O)—R, wherein R represents a linear or branched $C_1$-$C_6$ alkyl radical;
$R_a$, $R_b$ and $R_c$ are independently chosen from hydrogen atoms, halogen atoms, and $C_1$-$C_6$ alkyl radicals; and
X is chosen from:
i) an amino radical —NT₁T₂,
ii) an aminoalkylamino radical —N(T₃)-L-NT₁T₂ or
iii) an oxyalkylamino radical —O-L-NT₁T₂;
wherein T₁ and T₂ are independently chosen from linear or branched $C_1$-$C_6$ alkyl radicals optionally substituted with one or more hydroxyl radicals;
or T₁ and T₂ together form, with the nitrogen atom to which they are attached, a saturated or unsaturated heterocycle comprising 5 to 7 members, wherein one of the members of which may be a heteroatom chosen from O, S and N; wherein said heterocycle is optionally substituted with one or more linear or branched $C_1$-$C_4$ alkyl or linear or branched $C_1$-$C_4$ hydroxyalkyl radicals;
wherein T₃ is chosen from a hydrogen atom or a linear or branched $C_1$-$C_6$ alkyl radical optionally substituted with one or more hydroxyl radicals; and
L represents a linear or branched, saturated $C_1$-$C_{10}$ alkylene hydrocarbon-based chain optionally substituted with one or more hydroxyl radicals.

2. The method according to claim 1, wherein the compound of formula (I) comprises radicals R₁, R₂, R₃, R₄, R₅ and R₆ which are identical and which represent a hydrogen atom.

3. The method according to claim 1, wherein the compound of formula (I) comprises a radical X chosen from i) an amino radical —NT₁T₂.

4. The method according to claim 1, wherein the compound of formula (I) comprises a radical X chosen from ii) an aminoalkylamino radical —N(T₃)-L-NT₁T₂.

5. The method according to claim 1, wherein the compound of formula (I) comprises a radical X chosen from iii) an oxyalkylamino radical —O-L-NT₁T₂.

6. The method according to claim 1, wherein the compound of formula (I) comprises radicals T₁ and T₂ which are independently chosen from a linear or branched $C_1$-$C_4$ alkyl radical, optionally substituted with one or more hydroxyl radicals.

7. The method according to claim 1, wherein the compound of formula (I) comprises radicals T₁ and T₂ which together form, with the nitrogen atom which bears them, a heterocycle chosen from imidazole, pyridine, piperazine, pyrrolidine, morpholine, pyrimidine, benzimidazole and piperidine;
said heterocycle optionally substituted with one or more linear or branched $C_1$-$C_4$ alkyl or $C_1$-$C_4$ hydroxyalkyl radicals.

8. The method according to claim 1, wherein the compound of formula (I) comprises a radical X chosen from ii) an aminoalkylamino radical —N(T₃)-L-NT₁T₂, wherein T₃ is chosen from a hydrogen atom or a linear or branched $C_1$-$C_4$ alkyl radical.

9. The method according to claim 1, wherein the compound of formula (I) comprises a radical L chosen from a linear, saturated $C_1$-$C_6$ alkylene hydrocarbon-based chain, optionally substituted with one or more hydroxyl radicals.

10. The method according to claim 1, wherein the compound of formula (I) is chosen from at least one of compounds 1 to 28, salts thereof with organic or inorganic acids or bases, and/or solvates thereof:

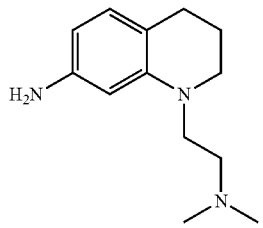

(A)

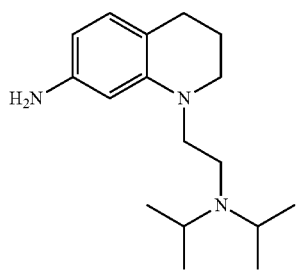

(B)

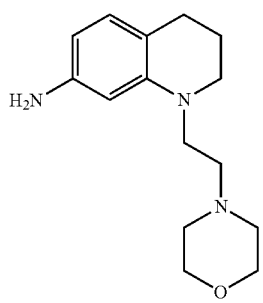

(C)

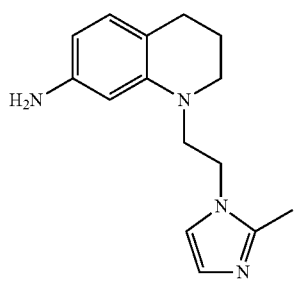

(D)

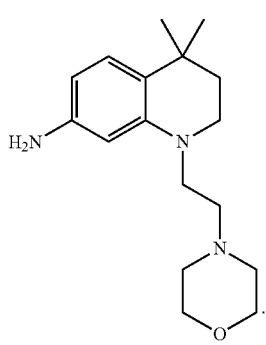

(E)

11. The method according to claim 1, wherein the process is carried out in the presence of at least one oxidation base and at least one oxidizing agent, for a time sufficient to develop the desired coloration, the oxidizing agent being applied before, simultaneously with, or after the application of the at least one compound of formula (I) and the at least one oxidation base.

12. A compound of formula (I):

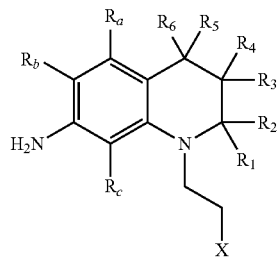

(I)

wherein:

$R_1$, $R_2$, $R_3$, $R_4$, $R_5$ and $R_6$ are independently chosen from:
i) hydrogen or halogen atoms;
ii) linear or branched $C_1$-$C_6$ alkyl radicals, optionally substituted with one or more hydroxyl groups;
iii) ($C_1$-$C_6$)alkoxycarbonyl radicals —C(O)—O—R, wherein R represents a linear or branched $C_1$-$C_6$ alkyl radical; and
iv) alkylcarbonyloxy radicals —O—C(O)—R, wherein R represents a linear or branched $C_1$-$C_6$ alkyl radical;

$R_a$, $R_b$, and $R_c$ are independently chosen from hydrogen atoms, halogen atoms, and $C_1$-$C_6$ alkyl radicals; and X is chosen from:
i) an amino radical —$NT_1T_2$,
ii) an aminoalkylamino radical —N($T_3$)-L-$NT_1T_2$ or
iii) an oxyalkylamino radical —O-L-$NT_1T_2$;
wherein $T_1$ and $T_2$ are independently chosen from linear or branched $C_1$-$C_6$ alkyl radicals optionally substituted with one or more hydroxyl radicals;
or $T_1$ and $T_2$ together form, with the nitrogen atom to which they are attached, a saturated or unsaturated heterocycle comprising 5 to 7 members, wherein one of the members of which may be a heteroatom chosen from O, S and N; wherein said heterocycle is optionally substituted with one or more linear or branched $C_1$-$C_4$ alkyl or linear or branched $C_1$-$C_4$ hydroxyalkyl radicals;
wherein $T_3$ is chosen from a hydrogen atom or a linear or branched $C_1$-$C_6$ alkyl radical optionally substituted with one or more hydroxyl radicals; and
L represents a linear or branched, saturated $C_1$-$C_{10}$ alkylene hydrocarbon-based chain optionally substituted with one or more hydroxyl radicals;
with the proviso that the compound of formula (I) cannot be chosen from compounds (A), (B), (C), (D) or (E):

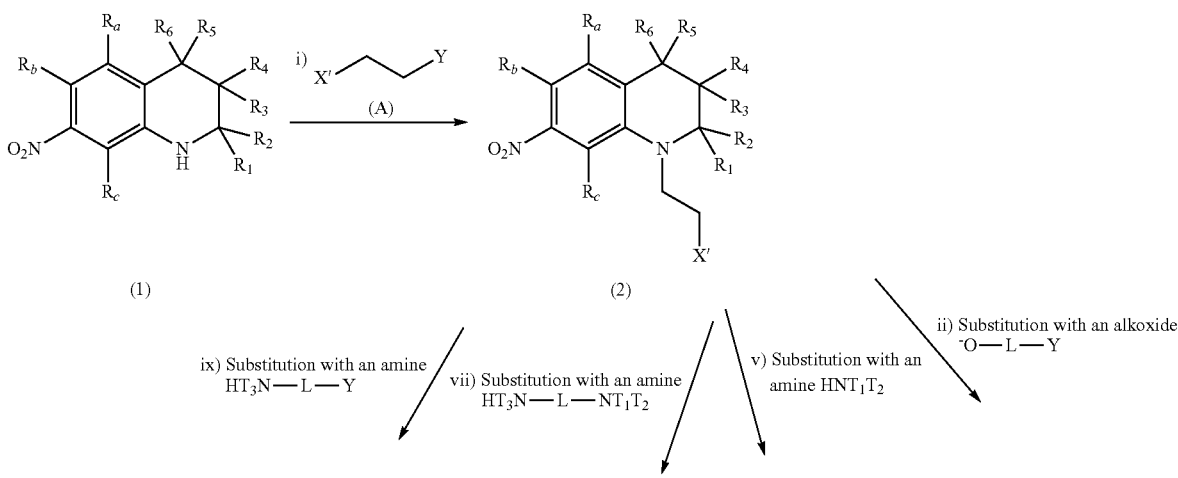

Scheme (1)

-continued

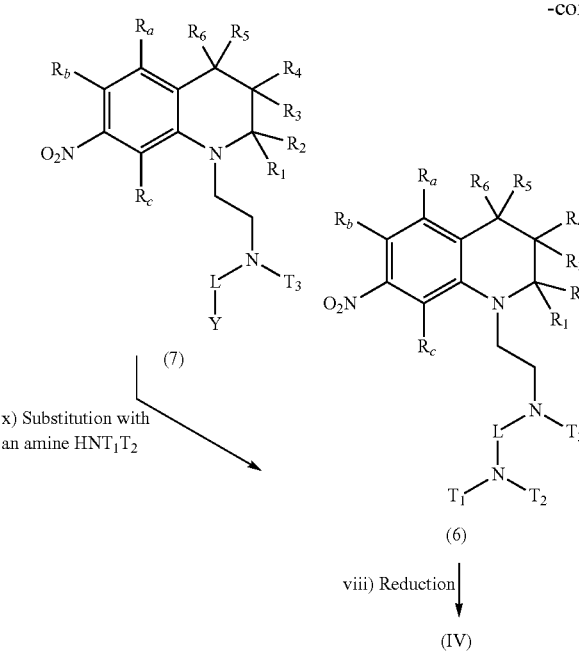

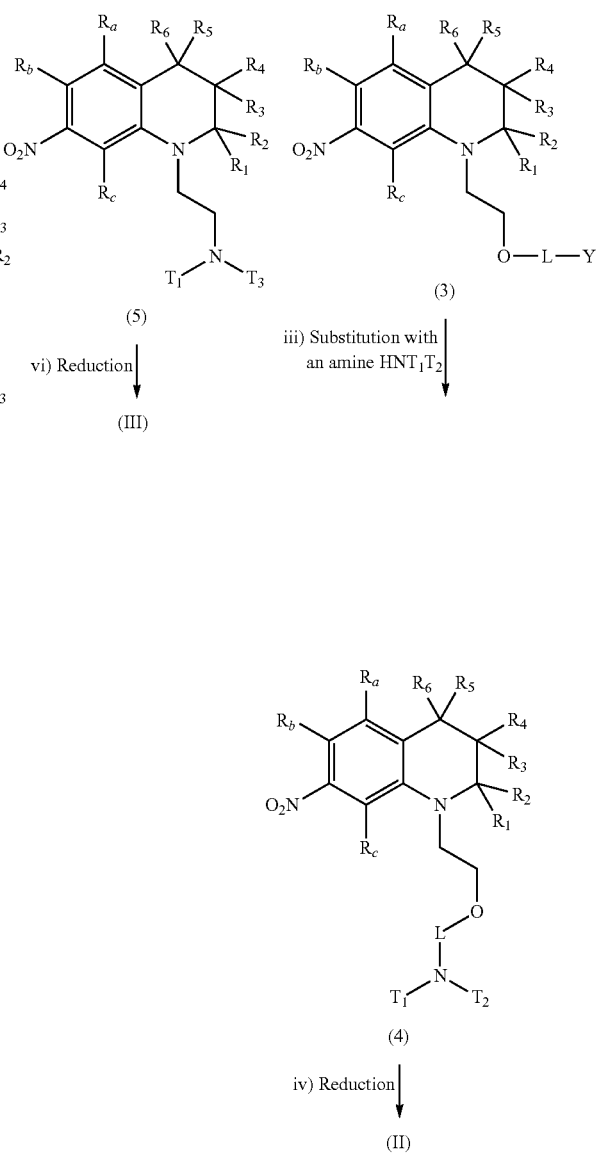

13. A composition comprising
i) at least one compound of formula (I)
ii) optionally at least one oxidation base, and
iii) optionally at least one oxidizing agent,
wherein the compound of formula (I) is:

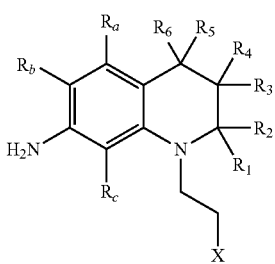

(I)

wherein:
$R_1$, $R_2$, $R_3$, $R_4$, $R_5$ and $R_6$ are independently chosen from:
  i) hydrogen or halogen atoms;
  ii) linear or branched $C_1$-$C_6$ alkyl radicals, optionally substituted with one or more hydroxyl groups;
  iii) ($C_1$-$C_6$)alkoxycarbonyl radicals —C(O)—O—R, wherein R represents a linear or branched $C_1$-$C_6$ alkyl radical; and
  iv) alkylcarbonyloxy radicals —O—C(O)—R, wherein R represents a linear or branched $C_1$-$C_6$ alkyl radical;
$R_a$, $R_b$ and IR, are independently chosen from hydrogen atoms, halogen atoms, and $C_1$-$C_6$ alkyl radicals; and
X is chosen from:
  i) an amino radical —$NT_1T_2$,
  ii) an aminoalkylamino radical —N($T_3$)-L-$NT_1T_2$ or
  iii) an oxyalkylamino radical —O-L-$NT_1T_2$;
  wherein $T_1$ and $T_2$ are independently chosen from linear or branched $C_1$-$C_6$ alkyl radicals optionally substituted with one or more hydroxyl radicals;

or $T_1$ and $T_2$ together form, with the nitrogen atom to which they are attached, a saturated or unsaturated heterocycle comprising 5 to 7 members, wherein one of the members of which may be a heteroatom chosen from O, S and N; wherein said heterocycle is optionally substituted with one or more linear or branched $C_1$-$C_4$ alkyl or linear or branched $C_1$-$C_4$ hydroxyalkyl radicals;

wherein $T_3$ is chosen from a hydrogen atom or a linear or branched $C_1$-$C_6$ alkyl radical optionally substituted with one or more hydroxyl radicals; and L represents a linear or branched, saturated $C_1$-$C_{10}$ alkylene hydrocarbon-based chain optionally substituted with one or more hydroxyl radicals;

with the proviso that the compound of formula (I) cannot be chosen from compounds (A), (B), (C), (D) or (E):

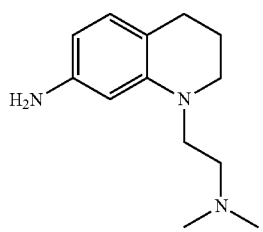
(A)

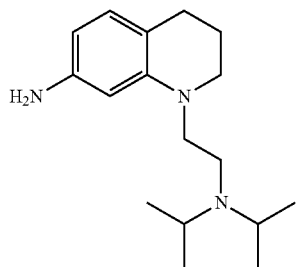
(B)

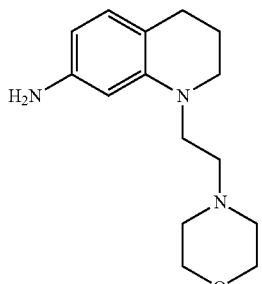
(C)

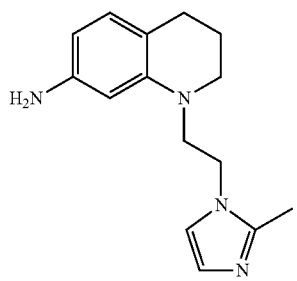
(D)

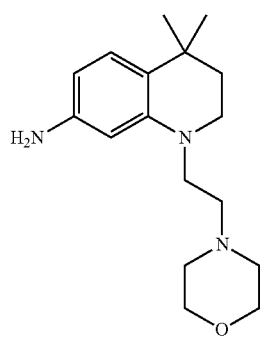
(E)

14. A composition according to claim 13, wherein the at least one oxidation base is chosen from paraphenylene-diamines and para-aminophenols.

15. A multi-compartment device comprising:
 a. a first compartment containing the composition according to claim 13, said composition being free of oxidizing agent, and
 b. a second compartment containing at least one oxidizing agent.

* * * * *

UNITED STATES PATENT AND TRADEMARK OFFICE
CERTIFICATE OF CORRECTION

PATENT NO. : 9,233,060 B2
APPLICATION NO. : 14/365722
DATED : January 12, 2016
INVENTOR(S) : Aziz Fadli It is certified that error appears in the above-identified patent and that said Letters Patent is hereby corrected as shown below:

Claims
Col. 38, line 21, through Col. 39, line 15, claim 10, delete entirely and insert the attached Compounds 1-28.

| | |
|---|---|
| 1-[2-(1H-imidazol-1-yl)ethyl]-1,2,3,4-tetrahydroquinolin-7-amine | 1-[2-(4-methylpiperazin-1-yl)ethyl]-1,2,3,4-tetrahydroquinolin-7-amine |
| 1 | 2 |
| 1-[2-(diethylamino)ethyl]-1,2,3,4-tetrahydroquinolin-7-amine | 1-[2-(pyrrolidin-1-yl)ethyl]-1,2,3,4-tetrahydroquinolin-7-amine |
| 3 | 4 |
| N'-[2-(7-amino-3,4-dihydroquinolin-1(2H)-yl)ethyl]-N,N-dimethylethane-1,2-diamine | 1-[2-(piperidin-1-yl)ethyl]-1,2,3,4-tetrahydroquinolin-7-amine |
| 5 | 6 |
| 1-(2-{[2-(pyrrolidin-1-yl)ethyl]amino}ethyl)-1,2,3,4-tetrahydroquinolin-7-amine | 1-[2-(morpholin-4-yl)ethyl]-1,2,3,4-tetrahydroquinolin-7-amine |
| 7 | 8 or (C) |

Signed and Sealed this
Fifth Day of July, 2016

Michelle K. Lee
*Director of the United States Patent and Trademark Office*

CERTIFICATE OF CORRECTION (continued)
U.S. Pat. No. 9,233,060 B2

| | |
|---|---|
| 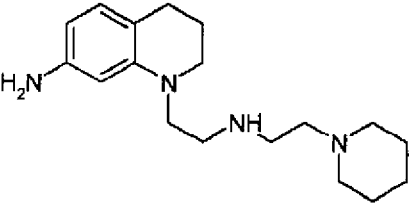<br>1-(2-{[2-(piperidin-1-yl)ethyl]amino}ethyl)-1,2,3,4-tetrahydroquinolin-7-amine | 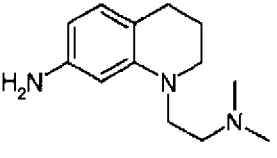<br>1-[2-(dimethylamino)ethyl]-1,2,3,4-tetrahydroquinolin-7-amine |
| 9 | 10 or (A) |
| 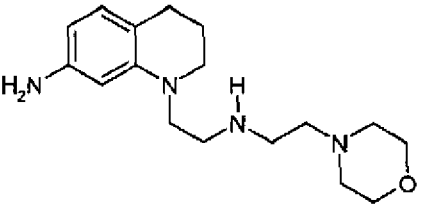<br>1-(2-{[2-(morpholin-4-yl)ethyl]amino}ethyl)-1,2,3,4-tetrahydroquinolin-7-amine | 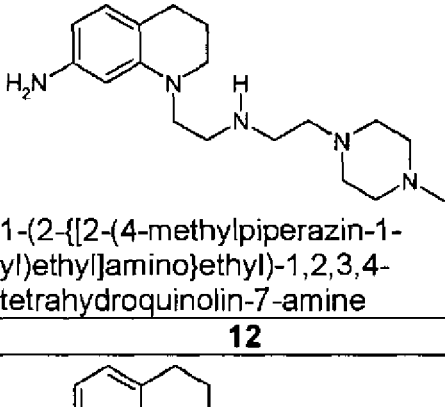<br>1-(2-{[2-(4-methylpiperazin-1-yl)ethyl]amino}ethyl)-1,2,3,4-tetrahydroquinolin-7-amine |
| 11 | 12 |
| 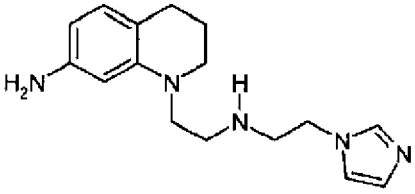<br>1-(2-{[2-(1H-imidazol-1-yl)ethyl]amino}ethyl)-1,2,3,4-tetrahydroquinolin-7-amine | 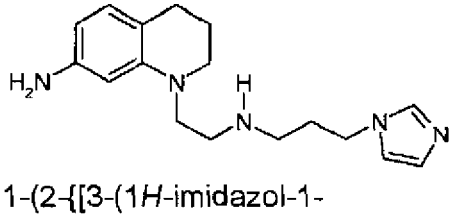<br>1-(2-{[3-(1H-imidazol-1-yl)propyl]amino}ethyl)-1,2,3,4-tetrahydroquinolin-7-amine |
| 13 | 14 |
| 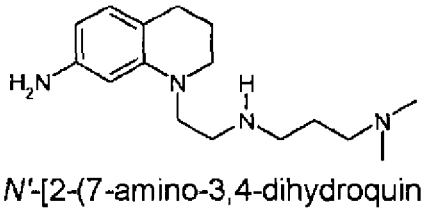<br>$N'$-[2-(7-amino-3,4-dihydroquinolin-1(2H)-yl)ethyl]-$N,N$-dimethylpropane-1,3-diamine | 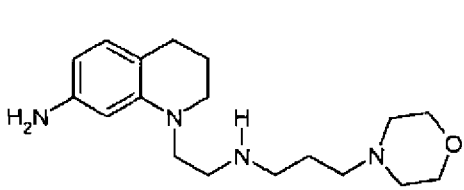<br>1-(2-{[3-(morpholin-4-yl)propyl]amino}ethyl)-1,2,3,4-tetrahydroquinolin-7-amine |
| 15 | 16 |

| | |
|---|---|
| 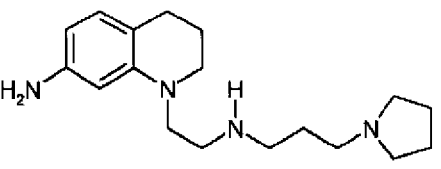<br>1-(2-{[3-(pyrrolidin-1-yl)propyl]amino}ethyl)-1,2,3,4-tetrahydroquinolin-7-amine | 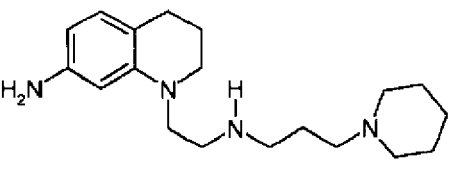<br>1-(2-{[3-(piperidin-1-yl)propyl]amino}ethyl)-1,2,3,4-tetrahydroquinolin-7-amine |
| 17 | 18 |
| 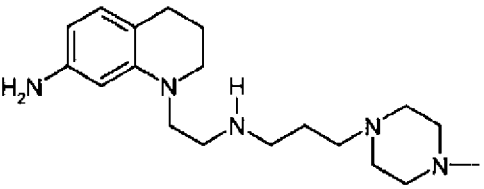<br>1-(2-{[3-(4-methylpiperazin-1-yl)propyl]amino}ethyl)-1,2,3,4-tetrahydroquinolin-7-amine | 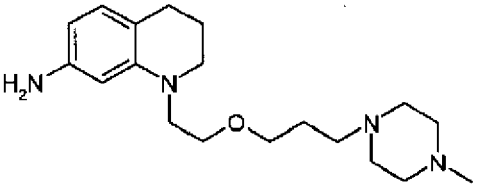<br>1-{2-[3-(4-methylpiperazin-1-yl)propoxy]ethyl}-1,2,3,4-tetrahydroquinolin-7-amine |
| 19 | 20 |
| 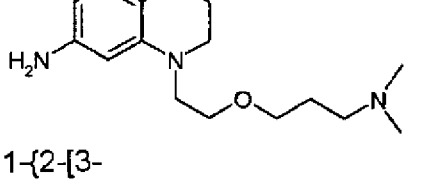<br>1-{2-[3-(dimethylamino)propoxy]ethyl}-1,2,3,4-tetrahydroquinolin-7-amine | 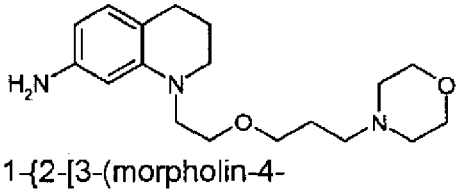<br>1-{2-[3-(morpholin-4-yl)propoxy]ethyl}-1,2,3,4-tetrahydroquinolin-7-amine |
| 21 | 22 |
| 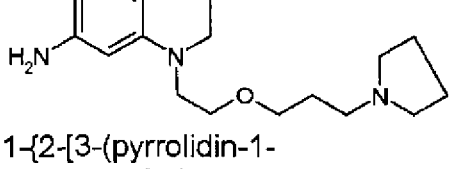<br>1-{2-[3-(pyrrolidin-1-yl)propoxy]ethyl}-1,2,3,4-tetrahydroquinolin-7-amine | 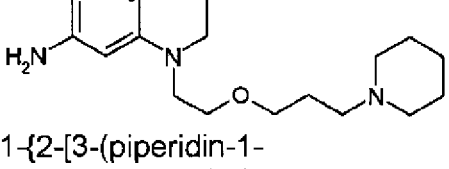<br>1-{2-[3-(piperidin-1-yl)propoxy]ethyl}-1,2,3,4-tetrahydroquinolin-7-amine |
| 23 | 24 |

CERTIFICATE OF CORRECTION (continued)

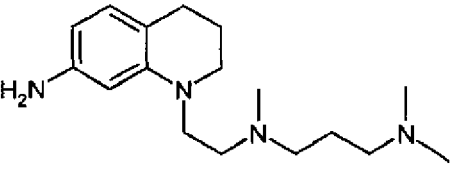

Col. 40, line 43, through Col. 41 and 42, line 48, claim 12, delete entirely and insert the attached compounds (A), (B), (C), (D), and (E).

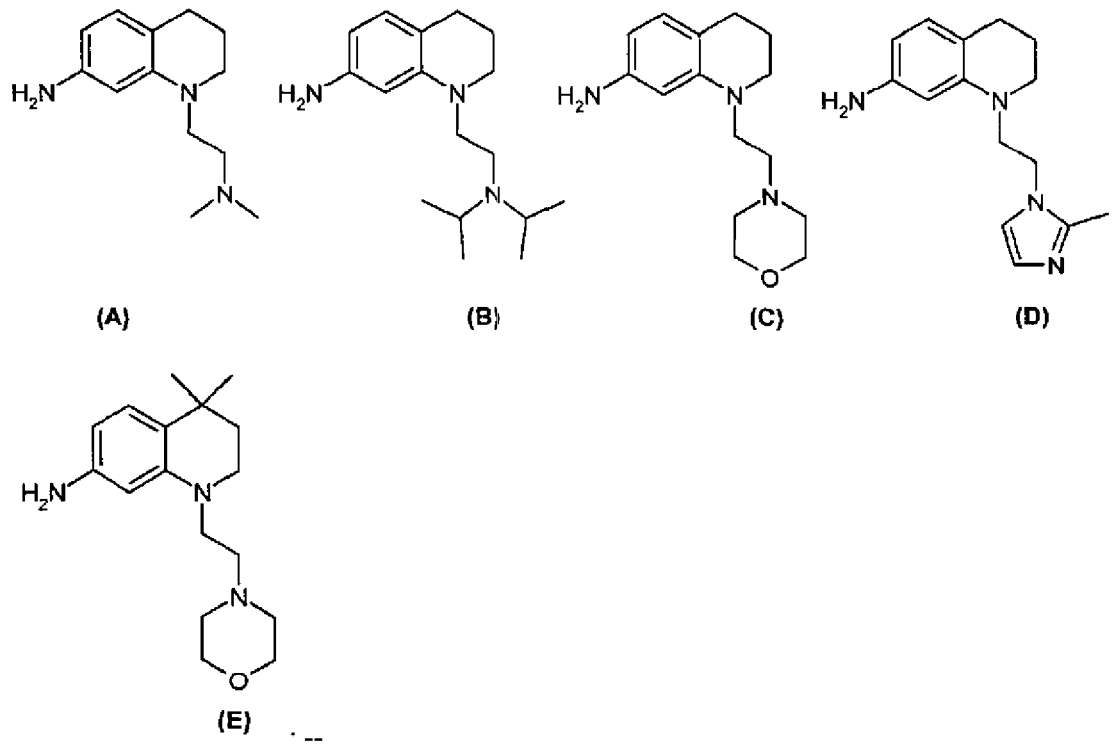

Col. 42, line 59, claim 13, change "IR" to -- Rc --.